United States Patent [19]

Pincus et al.

[11] Patent Number: 5,990,172
[45] Date of Patent: Nov. 23, 1999

[54] PEPTIDOMIMETICS FOR THE TREATMENT OF HIV INFECTION

[75] Inventors: Matthew R. Pincus, Brooklyn; Andrew S. Kende, Pittsford; Joseph J. Hlavka, Tuxedo Park, all of N.Y.; Henry B. Abajian, Hillsdale, N.J.

[73] Assignee: Innapharma, Inc., Suffern, N.Y.

[21] Appl. No.: 08/807,473

[22] Filed: Feb. 27, 1997

Related U.S. Application Data

[60] Provisional application No. 60/012,396, Feb. 28, 1996.

[51] Int. Cl.$^6$ ........................ A61K 31/165; C07C 233/05
[52] U.S. Cl. ......................... 514/621; 514/545; 514/681; 514/724; 514/730; 560/51; 560/53; 564/169; 568/327; 568/808
[58] Field of Search ..................................... 564/169, 170, 564/171, 172; 514/621, 545, 681, 724, 730; 560/51, 53; 568/327

[56] References Cited

U.S. PATENT DOCUMENTS

| | | | |
|---|---|---|---|
| 4,442,090 | 4/1984 | Kakeya et al. | 424/178 |
| 4,835,192 | 5/1989 | Johnson et al. | 514/729 |
| 5,162,499 | 11/1992 | Trampota et al. | 530/328 |
| 5,210,228 | 5/1993 | Todd et al. | 549/292 |
| 5,276,016 | 1/1994 | Pert et al. | 514/15 |
| 5,308,864 | 5/1994 | Lewis et al. | 514/460 |

FOREIGN PATENT DOCUMENTS

| | | |
|---|---|---|
| 88/09338 | 12/1988 | European Pat. Off. . |
| 579363 A1 | 1/1994 | European Pat. Off. . |
| 5085931 | 6/1993 | Japan . |

OTHER PUBLICATIONS

CA 63:4341 h, 1965.
Abdel–Meguid, S.S. et al. (1994), "An Orally Biovailable HIV–1 Protease Inhibitor Containing an Imidazole–Derived Peptide Bond Reaplcement: Crystallographic and Pharma-cokinetic Analysis," Biochemistry 33(39):11671–11677.
Ayuso, J.L. (1994), "Use of Psychotropic Drugs in Patients with HIV Infection," Drugs 47(4):599–610.
Brenneman et al. (1988), "Peptide T Sequences Prevent Neuronal Cell Death Produced by the Envelope Protein (gp120) of the Human Immunodeficiency Virus," Drug Dev. Res. 15(4):361–369.
Buzy et al. (1992), "Potent gp120–like neurotoxic activity in the cerebrospinal fluid of HIV–infected individuals is blocked by peptide T," Brain Res. 598:10–18.
Caglioti (1996), "The reduction of tosylhydrazones and of acyl tosylhydrazides," Tetrahedron 22:487–493.
Carucci, J.E. et al. (1989), "Blocking of the nucleotide exchange of the P21 protein with an active site affinity label," Med. Sci. Res. 17:559–560.
Chen (1989), "Comparitive X–ray Crystallographic Evidence for a β–Bend Conformation as the Active Structure for Peptide T in T4 Receptor Recognition," J. Protein Chem. 8:87–100.
Connell, E.V. et al. (Feb. 1994), "Combinative interactions of a human immunodeficiency virus (HIV) Tat antagonist with HIV reverse transcriptase inhibitors and an HIV protease inhibitor," Antimicrob. Agents Chemother. (US) 38 (2):348–52.
Dorsey, B.D. et al. (1994), "The Design of a Potent and Orally Bioavailable HIV Protease Inhibitor," J. Med. Chem. 37:(21):3443–3451.
Dreiding et al. (1955), "A Synthesis of trans–10–Methyl–2–decalone," J. Am. Chem. Soc. 77:411–414.
Ito et al. (1978), "Synthesis of α,β–Unsaturated Carbonyl Compounds by Palladium (II)–Catalyzed Dehydrosilylation of Silyl Enol Ethers," J. Org. Chem. 43:1011–1013.
Kende et al. (1982), "Stereospecific Total Synthesis of Ajugarin–IV," Tet. Letts. 23:1751–1754.
Kim et al. (1994), "A new hydroxyethylamine class of HIV–1 protease inhibitors with high antiviral potency and oral bioavailabilty," Bioorg. Med. Chem. Letts. 4(19):2273–2278.
Licht, D. et al. (1992), "Correlation of the Conformation of a Modified Ribonuclease Octapeptide, Homologous to Peptide T, with Its Ability to Indice CD4–Dependent Monocyte Chemotaxis," J. Protein Chem. 11:475–481.
Marastoni et al. (1992), "A cyclic peptide T anaogue with high chrmotactic activity," Eur. J. Med. Chem. 27:383–389.
Marshall et al. (1970), "The Stereoselective Total Synthesis of Racemic Nootkatone," Tetrahedron Lett., No. 15, p. 1239.
McDougal et al. (1985), "Immunoassay for the dettection and Quantitation of Infectious Human Retrovirus, Lymphad-enopathy–Associated Virus (LAV)," J. Immun. Meth. 76:171–183.
McMurry et al. (1976), "Ester Cleavages Via SN2–Type Dealkylation," Org. React. 24:187–224.
Oikawa et al. (1975), "An Application of Reactions of β–Ketosulfoxides to Estrone Synthesis," Chem. Pharm. Bull. 23:2466–2467.

(List continued on next page.)

*Primary Examiner*—Shailendra Kumar
*Attorney, Agent, or Firm*—Greenlee, Winner and Sullivan, P.C.

[57] ABSTRACT

This invention provides peptidomimetics which bind to T4 or CD4 cell receptors and are useful in inhibiting viral infectivity by viruses which bind to T4 cell receptors. More specifically, peptidomimetics of this invention can alleviate symptoms of AIDS by inhibiting binding of HIV, the virus associated with AIDS, to receptor sites in human cells susceptible to HIV infection. These peptidomimetics, in particular, inhibit binding of HIV to cells of brain membrane and the immune system. They also display substantially longer half-lives in vivo than peptide T. The compounds of this invention which bind to T4 or CD4 receptors and thereby inhibit binding of HIV, alone or in combination with one another, can be used to alleviate AIDS symptoms and ameliorate symptoms of HIV infection, especially neuronal dementias and Kaposi's sarcoma. The compounds of this invention, alone or in combination, can further be used to prevent development of AIDS in persons who might become exposed to HIV.

29 Claims, No Drawings

OTHER PUBLICATIONS

Oritani et al. (1984), "Enantioselectivity of Microbial Hydrolysis of (±)–Decahydro–2–napththyl Acetatos. Preparations and Absolute Configurations of Chiral Decahydro2–naththols," J. Org. Chem. 49:3689–3694.

Pert et al. (1986), "Octapeptides deduced from the neuropeptide receptor–like pattern of antigen T4 in brain potently inhibit human immunodeficiency virus receptor binding and T–cell infectivity," Proc. Natl. Acad. Sci. USA 83:9254–9258.

Roberts et al. (1990), "Rational Design of Peptide–Based HIV Proteinase Inhibitors," Science 248:358–361.

Ruff et al. (1987), "CD4 receptor binding peptides that block HIV infectivity cause human monocyte chemotaxis," FEBS Lett. 211:17–22.

Ruff et al. (Sep. 26, 1987), "Peptide $T_{[4-8]}$ is Core HIV Envelope Sequence Required for CD4 Receptor Attachment," Lancet, p. 751.

Ruff et al. (1991), "Pharmacokinetics of Peptide T in Patients with Acquired Immunodeficiency Syndrome (AIDS)," Prog. Neuro–Psychopharmacol. & Biol. Psychiat. 15:791–801.

Schinazi et al. (1986), "Delayed Treatment with Combinations of Antiviral Drugs in Mice Infected with Herpes Simplex Virus and Application of the Median Effect Method of Analysis," Antimicrob. Agents Chemother. 30:491–498.

Schinazi et al. (1988), "Combinations of Isoprinosine and 3'–Azido–3'–Deoxythymidine in Lymphocytes Infected with Human Immunodeficiency Virus Type 1," Agents Chemother. 32:1784–1787.

Sodroski et al. (Jun. 20, 1987), "HIV Envelope–CD4 Interaction Not Inhibited by Synthetic Octaptpdies," Lancet, pp. 1428–1429.

Spira et al. (1987), "Micromethod for Assaying Reverse Transcriptase of Human T–Cell Lymphotropic Virus Type III/Lymphadenopathy–Associated Virus," J. Clin. Microbiol. 25:97–99.

Tsuda, Y. and Sakai, Y. (1981), "Efficient Dealkoxycarbonylation of Some β–Ketoesters by Halides of Group IIa Metals," Synthesis, pp. 119–120.

PEPTIDOMIMETICS FOR THE TREATMENT OF HIV INFECTION

CROSS-REFERENCE TO RELATED APPLICATIONS

This application takes priority from U.S. provisional application Ser. No. 60/012,396 under 35 U.S.C. 119(e) filed Feb. 28, 1996, which is incorporated in its entirety by reference herein.

FIELD OF THE INVENTION

This invention generally relates to antiviral agents and more particularly to chemical compounds which function as peptidomimetics of peptide T and thereby inhibit binding of viruses to T4 receptors. These peptidomimetics are useful in inhibiting viral infection and in the treatment of symptoms of viral infection, most particularly in inhibiting infection by HIV and in the treatment of symptoms of HIV infection.

BACKGROUND OF THE INVENTION

Acquired Immune Deficiency Syndrome (AIDS) is believed to be caused by the Human Immunodeficiency Virus (HIV) family of retroviruses. The retrovirus attacks and ultimately destroys the host's cell-mediated immune system. In the human cell-mediated immune system, T cells and macrophages are key to recognition of infectious agents. T cells have surface receptors that recognize either the combination of "processed" (i.e., partially digested) antigen with histocompatibility markers on antigen-presenting cells or the combination of unprocessed "superantigens" with part of the histocompatibility marker on the antigen presenting cells. T cells interact with and cause macrophages to engulf and destroy a recognized infectious agent. Both T cells and macrophages have T4 (or CD4) receptors on their surfaces. It is known that HIV infects a cell by binding to T4 receptor after which it enters the cell by endocytosis. The HIV genome is then transcribed to DNA by its own by its own reverse transcriptase (RT), and integrated into the host cell genome. Replication of the virus in the cell ultimately destroys the cell.

During the HIV latency period, which can extend many years, the host's helper T4 lymphocytes die off, rendering the host increasingly susceptible to various bacterial and other infections. Infected lymphocytes secrete an oncoprotein, which drives tumorigenesis/angiogenesis in AIDS-associated Kaposi's sarcoma (KS).

In addition to symptoms arising from immunodeficiency, patients with AIDS show neuropsychological defects. Eventually AIDS-associated damage to the brain and the central nervous system also occurs. The central nervous and immune systems share a large number of specific cell-surface recognition molecules which serve as receptors for neuropeptide-mediated intercellular communication. In particular, the central nervous system has CD4 cell-surface recognition molecules.

HIV attachment to the T4 (CD4) receptor occurs via the viral coat protein gp120. This protein has also been shown to affix covalently to cells of the immune system as well as to the brain membranes of humans, rats, and monkeys. A portion of gp120, an octapeptide called peptide T, binds to the T4 receptor in vitro and block attachment of the virus to the CD4 receptors of T cells, monocytes and cells of the central nervous system that express CD4 receptor. Peptide T has high affinity for CD4 receptors of T cells and monocytes with dissociation constants in the low nanomolar range. See, Pert et al. (1986) Proc. Natl. Acad. Sci. USA 83, 9254–9258; Ruff et al. (1987a) FEBS Lett., 211:17–22; Ruff et al. (1987b) Lancet September 26:751. Several peptides from the coat proteins of other viruses also exhibit high affinity for binding to CD4. See, Ruff et al. (1987a) and Ruff et al. (1987b).

In several clinical protocol trials for patients with AIDS, peptide T was reported to effect significant amelioration of AIDS symptoms, including AIDS-related dementias. Buzy et al. (1992) Brain Research 598: 10–18. The effect in AIDS-related dementias may result from blocking HIV attack on the CD4 positive cells of the central nervous system. Peptide T also protects against gp120 protein induced neuronal death. Benneman et al. (1988) Drug Dev. Res. 15(4): 361–370.

One problem with the use of peptide T in the treatment of AIDS is its short half-life (10–60 minutes) which greatly reduces its efficacy. Ruff et al. (1991) Prog. Neuro-Pyschopharmacol. & Biol. Psychiat. 15: 791–799.

One of the few agents reported useful clinically for HIV is AZT, 3'-azido-3'-deoxythymidine, a nucleoside chain terminator in transcription. However, the clinical benefits of AZT have not yet been definitively established. AZT induces drug resistance by mutating the HIV Reverse Transcriptase (RT) and it is severely toxic to the host. Current practice, also as yet without proven efficacy, employs a combination therapy using mixed nucleosides at lower doses.

A number of compounds have been reported to inhibit HIV activity or replication, including HPA-23, interferons, ribavirin, phosphonoformate, ansamycin, suramin, imuthiol, penicillamine, rifabutin, AL-721, 2',3'-dideoxycytidine (DDC), 2',3'-dideoxyadenosine (DDA), 3'-azido-2',3'-dideoxyuridine (AzddU),2',3'-didehydrocytidine, 3'-deoxy-2',3'-didehydrothymidine and 3'-azido-5-ethyl-2',3'-dideoxyuridine (AzddEU). While each of these compounds may have a place in the therapeutic regimen for AIDS patients, none are wholly effective in blocking HIV infection, reversal of symptoms, or major amelioration of the disease course. Many of these agents are significantly toxic and produce major side effects which limit their utility.

Recently, diazepines have been reported active against HIV RT and Trans-Activator Gene Protein (Tat). Cornell, E. et al. 33rd Interscience Conference on Antimicrobral Agents and Chemotherapy, New Orleans, La., Oct. 17–20, 1993 (Program and Abstracts); Ayuso, J. L. (1994) Drugs 47(4): 599–610. Inhibitors of the HIV protease have also been developed. See: Abdel-Meguid, S. S. et al. (1994) Biochemistry 33(39): 11671–11677; Dorsey, B. D. et al. J. Medicinal Chem. (1994) Bioorg. Med. Chem. Letts. 4(19): 2343–2346; Kim et al. (1994) Bioorg. Med. Chem. Letts. 4(19): 2273–2278.

There remains a great need for alternative agents, particularly non-nucleoside and non-peptide drugs, which will effectively inhibit HIV activity and replication and yet produce fewer undesired side effects. Of particular, interest in view of the inhibitory activity of peptide T are non-peptide agents which mimic its binding affinity for T4 (CD4) receptors.

SUMMARY OF THE INVENTION

This invention provides peptidomimetics which bind to T4 or CD4 cell receptors and are useful in inhibiting viral infectivity by viruses which bind to T4 cell receptors. More specifically, peptidomimetics of this invention can alleviate symptoms of AIDS by inhibiting binding of HIV, the virus associated with AIDS, to receptor sites in human cells susceptible to HIV infection. These peptidomimetics, in particular, inhibit binding of HIV to cells of brain membrane and the immune system. They also display substantially longer half-lives in vivo than peptide T. The compounds of this invention which bind to T4 or CD4 receptors and thereby inhibit binding of HIV, alone or in combination with one another, can be used to alleviate AIDS symptoms and ameliorate symptoms of HIV infection, especially neuronal dementias and Kaposi's sarcoma. The compounds of this invention, alone or in combination, can further be used to prevent development of AIDS in persons who might become exposed to HIV.

Further, the compounds of this invention which bind to T4 or CD4 receptors can be used in binding assays to detect the presence of such receptors and to label and enumerate cells having such receptors. In such assays, T4 binding compounds can be detected and quantitated by conventional analytical methods or more preferably radiolabelled or provided with fluorescent labels. The compounds of this invention can also be used in competitive binding assays to identify other compounds which bind to T4 or CD4 receptors.

Most generally, peptidomimetics which bind T4 or CD4 receptors are substituted decalins and octalones, and enantiomers thereof, of formula:

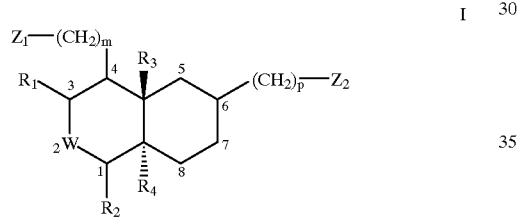

I where $R_1$ is a hydrogen, R', HO, R'O, ether group R'O—$(CH_2)_q$, or a carboxy-containing group QCO—$(CH_2)_q$, where q an integer from 0 to about 5, and where Q is R', R'O, R'S, or R'R"N; $Z_1$ and $Z_2$, independently of one another, are $R_5R_6N$, $R_7O$, or $R_8S$ groups and m and p are integers from 1 to about 5; $R_3$ and $R_4$, independently of one another, are a hydrogen, an alkyl group or an unsaturated alkyl group; $R_2$ can in general be any hydrocarbyl or substituted hydrocarbyl group, as defined infra, and W is a $CH_2$, a CH—OH (either isomer) or a C=O group. Substituents R', R" and $R_5$–$R_8$, most generally and independently of one another, can be a hydrogen, a hydrocarbyl or substituted hydrocarbyl group. R' and R" are preferably hydrogen, an alkyl, substituted alkyl, unsaturated alkyl, substituted unsaturated alkyl group, aryl or substituted aryl and more preferably are hydrogen or an alkyl group. R' and R" alkyl and unsaturated alkyl groups preferably have from 1 to about 7 carbon atoms. $R_5$–$R_8$ are preferably hydrogen, alkyl, or unsaturated alkyl groups. More preferred $R_5$–$R_8$ are hydrogens or alkyl groups. Preferred $R_5$–$R_8$ alkyl groups are those having from 1 to about 7 carbon atoms. Most preferred R', R" and $R_5$–$R_8$ are hydrogen, and lower alkyl or lower unsaturated alkyl groups having from 1 to about 3 carbon atoms.

The ring numbering illustrated in Formula 1 is used hereinafter to reference substituent placement and other structural features of the compounds of this invention.

More preferred compounds of formula I are those isomers and enantiomers thereof having the structure II:

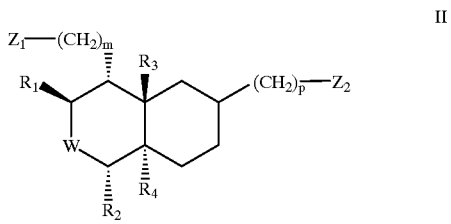

II

More specifically this invention provides compounds of formulas III–XII and IIIA–IVA, XA–XIIA, as well as compounds of formulas 9–11 and 29–31 and enantiomers thereof, which bind T4 or CD4 receptors and are useful in assays and to inhibit HIV infection as described above.

Compounds of formula III, and enantiomers thereof, are provided:

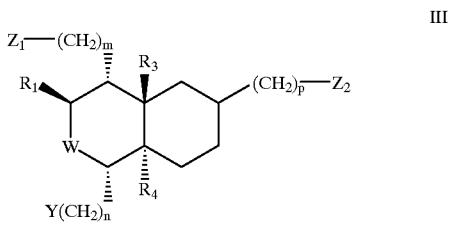

III

In addition, compounds of formula IIIA with stereoconfiguration at ring position 6 is specified and enantiomers thereof are provided:

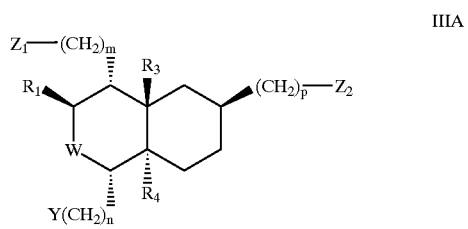

IIIA where $R_1$, $R_3$, $R_4$, $R_5$–$R_8$, R', R", $Z_1$, $Z_2$, m, p and q are as defined for formula I; Y is an aryl group which optionally can be substituted; and n is an integer from 1 to about 5. $Z_1$ and $Z_2$ are preferably $R_7O$, wherein $R_7$ is preferably a hydrogen or an alkyl group. Preferred $R_7$ alkyls are those having one to about 7 carbon atoms; more preferred alkyls are lower alkyls, i.e. those having 1 to about 3 carbon atoms. In compounds of formulas III and IIIA, $Z_1$ and $Z_2$ are more preferably OH groups, and p is more preferably an integer from 1 to about 3. Y is preferably an aryl or substituted aryl group having one or two aromatic rings, including fused rings, and is most preferably a 4-hydroxyphenyl group. $R_3$ and $R_4$ are preferably hydrogen or a methyl group.

Compounds of formula IV–VI, IVA–VIA, and enantiomers thereof are provided:

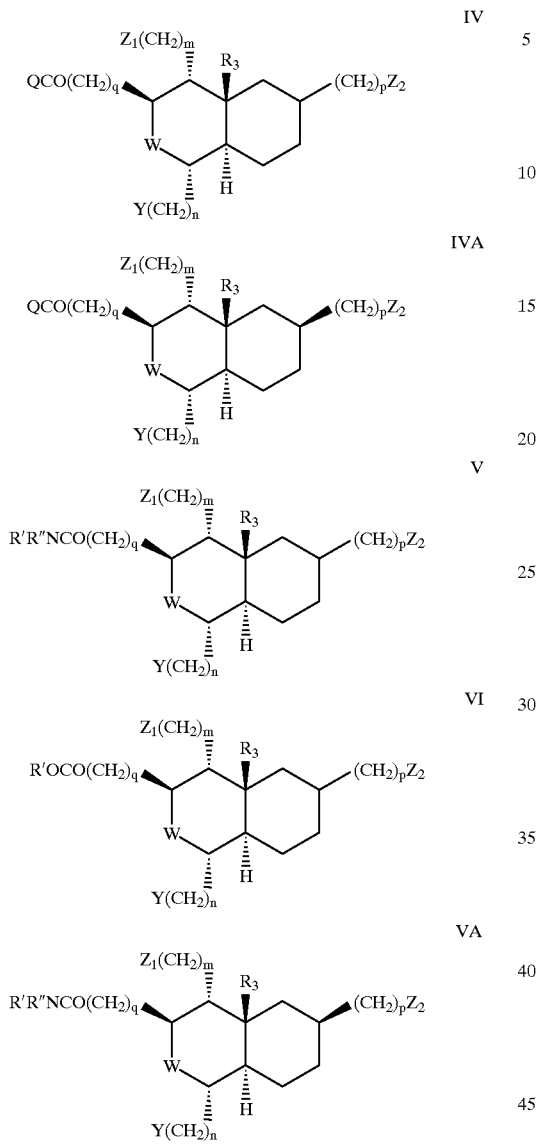

Compounds of formulas VII–IX and enantiomers thereof are also provided:

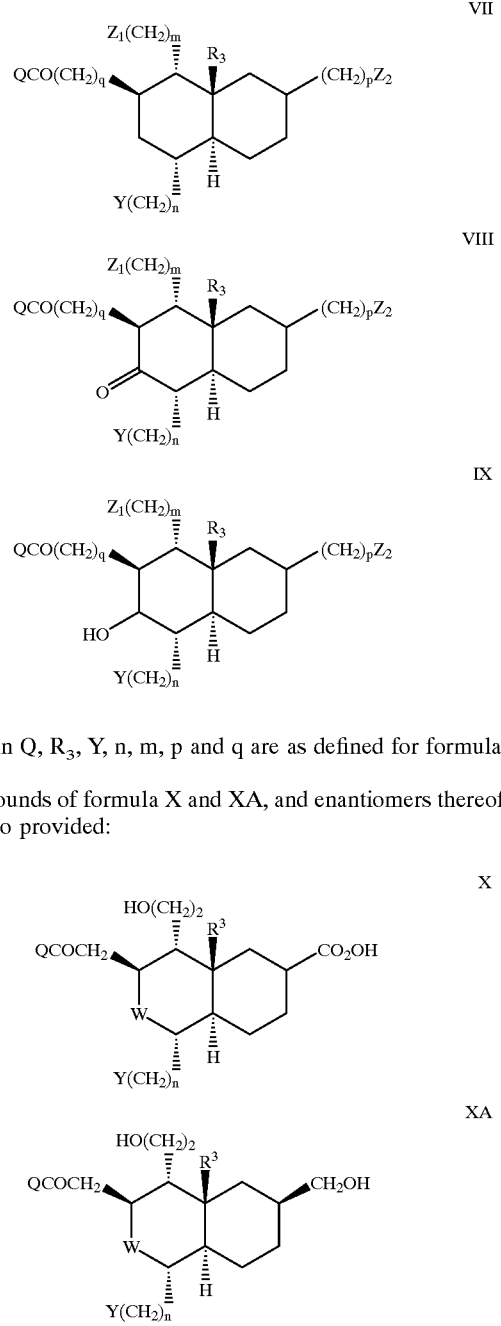

wherein Q, $R_3$, Y, n, m, p and q are as defined for formulas I–V.

Compounds of formula X and XA, and enantiomers thereof, are also provided:

wherein $R_3$, $R_5$–$R_8$, R', R", $Z_1$, $Z_2$, n, m, p and q are as defined for formulas I–III; and Y is an aryl or substituted aryl group. Integers n, p and m are more preferably one to three. $Z_1$ and $Z_2$ are more preferably $OR_7$. $R_7$ is preferably a hydrogen or alkyl group. R' and R", independently of one another, are a hydrogen atom or an alkyl group. Preferred $R_7$ alkyls have 1 to about 7 carbon atoms. $R_3$ is more preferably a hydrogen or a methyl group. Integer q is more preferably 1, 2 or 3. The Ar group preferably has 1 or 2 aromatic rings and more preferably is a phenyl group. Preferred aryl substituents are hydrogens, alkyl groups, more preferably those aklyl groups having from 1 to about 7 carbon atoms, inclusive, halogen atoms, more preferably fluorine atoms, $R_9O$ or $R_{10}S$, where $R_9$ and $R_{10}$ are independently a hydrogen or an alkyl group, more preferably those alkyl groups having from 1 to about 7 carbon atoms, inclusive. In compounds of formula IV, VI, IVA and VIA, Ar is most preferably a 4-hydroxyphenyl group.

wherein $R_3$, Y, Q and n are as defined above.

Compounds of formula I–X where n is 1 or 2 and Y is:

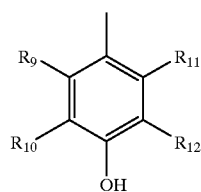

wherein $R_9$–$R_{12}$ substituents for the phenyl ring are preferred. $R_9$–$R_{12}$ are independently selected from the group of a hydrogen, a halogen, an alkyl group having from 1 to about 7 carbon atoms, OH, SH, $OR_{13}$ and $SR_{14}$ where $R_{13}$ and $R_{14}$ are, independently, alkyls having from 1 to 7 carbon atoms. Preferred alkyl groups for aryl ring substituents are lower alkyls having 1 to about 3 carbon atoms. In compounds of formula I–X and IIIA–VIA and XA preferred, $R_9$–$R_{12}$ are H. Compounds of formula XI and XIA, and enantiomers thereof, are also provided:

XI

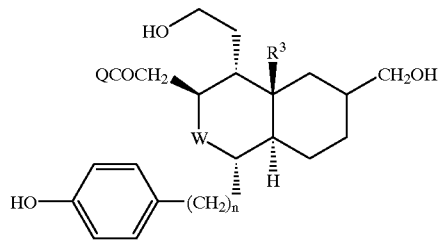

XIA

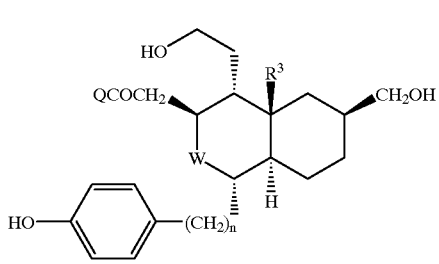

wherein $R_3$, Q, W, and n are as defined above.

More specifically compounds of formulas XIIA–XVA and XIIB–XVB, and enantiomers thereof, where n is 1 or 2 are provided:

XIIA

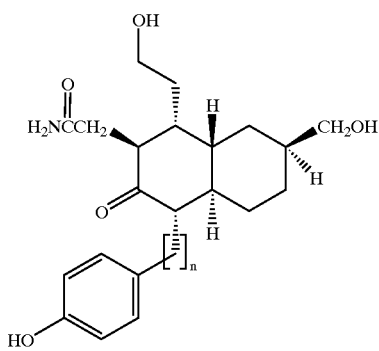

XIIB

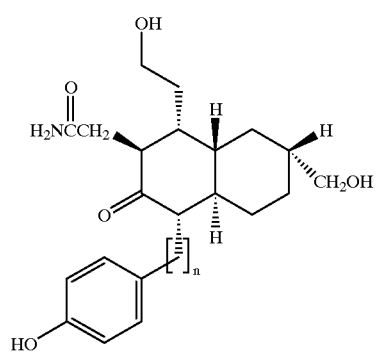

XIIIA

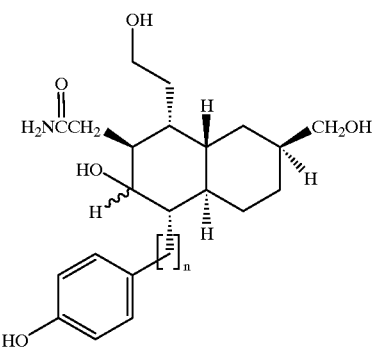

XIIIB

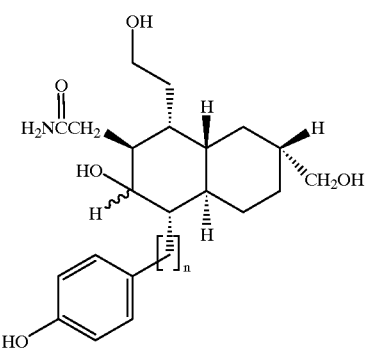

XIVA

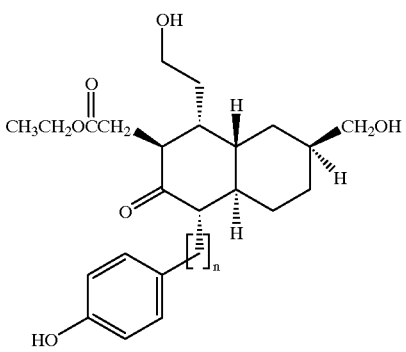

XIVB

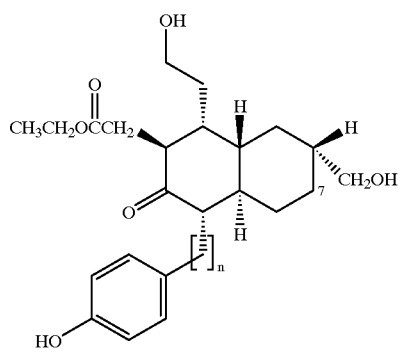

-continued

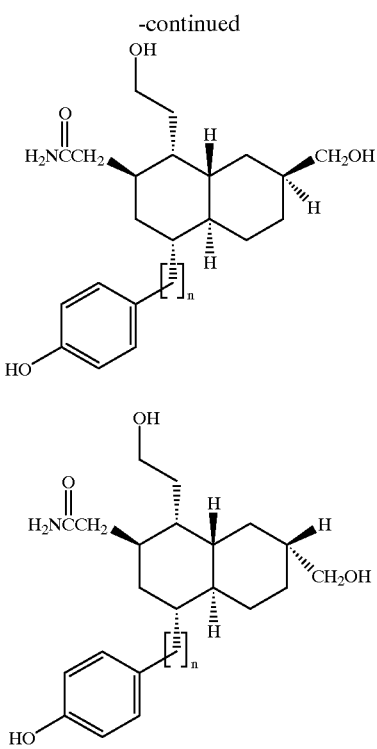

XVA

XVB

This invention further provides substituted cyclohexanes and cyclohexanones of formula XVI and XVIA:

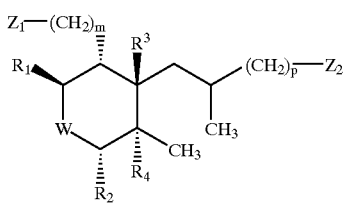

XVI

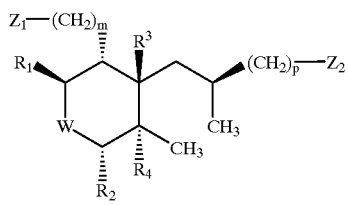

XVIA wherein the variables shown are as defined generally in formula I and can take those values defined in formulas I–XV.

The present invention also encompasses pharmaceutically acceptable acid addition salts and esters, if any, of the compounds of formulas I–XI, IIIA–XIA, XIIA–XVA, XIIB–XVB, XVI and XVIA.

This invention also provides pharmaceutical compositions useful in the treatment of AIDS symptoms and the inhibition of HIV infection. Such compositions comprise one or more of the peptidomimetic decalins or octalones of formula I or cyclohexane or cyclohexanones of formula XVI or XVIA and a pharmaceutically acceptable carrier or excipient adapted for use in human or veterinary medicine. Such compositions may optionally contain one or more other therapeutic agents or otherwise active ingredients, including one or more different antiviral agents, antimicrobial agents or preservatives. Pharmaceutical compositions of this invention can be formulated for any known means of human or animal administration including without limit for oral, buccal, parenteral, topical or rectal administration.

DETAILED DESCRIPTION OF THE INVENTION

Definitions

The term "hydrocarbyl" is used herein to refer generally to organic radicals comprised of carbon chains to which hydrogen and other elements are attached. $CH_2$ or CH groups and C atoms of the carbon chains of the hydrocarbyl may be replaced with one or more heteroatoms (i.e., non-carbon atoms) with the exception that the hydrocarbyl group is attached to the base ring structure of the compound via a bond to carbon. Suitable heteroatoms include but are not limited to O, S and N atoms. The term hydrocarbyl includes, but is not limited to alkyl, alkenyl, alkynyl, ether, thioether, aminoalkyl, hydroxylalkyl, thioalkyl, aryl and heterocyclic aryl groups, groups which have a mixture of saturated and unsaturated bonds, carbocyclic rings and combinations of such groups. The term also includes straight-chain, branched-chain and cyclic structures or combinations thereof. Hydrocarbyl groups are optionally substituted. Hydrocarbyl substitution includes substitution at one or more carbons in the group by moieties containing heteroatoms. Suitable substituents for hydrocarbyl groups include but are not limited to OH, SH, $NH_2$, COH, $CO_2H$, $OR_a$, $SR_a$, $NR_aR_b$, $CONR_aR_b$, and halogens, particularly fluorines, where $R_a$ and $R_b$ independently are alkyl, unsaturated alkyl or aryl groups.

The term "alkyl" takes its usual meaning in the art and is intended to include straight-chain, branched and cycloalkyl groups. The term includes, but is not limited to, methyl, ethyl, n-propyl, isopropyl, n-butyl, sec-butyl, isobutyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, and 1-methyl-1-propylbutyl. Alkyl groups are optionally substituted. Lower alkyl groups include amongothers methyl, ethyl, n-propyl, and isoprophyl groups.

The term "cycloalkyl" refers to alkyl groups having a hydrocarbon ring, particularly to those having rings of 3 to 7 carbon atoms. Cycloalky groups include those with alkyl group substitution on the ring. Cycloalkyl groups can include straight-chain and branched-chain portions. Cycloalkyl groups include but are not limited to cyclopropyl, cyclobutyl, cyclopentyl, cyclohexyl, cycloheptyl, cyclooctyl, and cyclononyl. Cycloalkyl groups can optionally be substituted.

The term "unsaturated alkyl" group is used herein generally to include alkyl groups in which one or more carbon-carbon single bonds have been converted to carbon-carbon double or triple bonds. The term includes alkenyl and alkynyl groups in their most general sense. The term is intended to include groups having more than one double or triple bond, or combinations of double and triple bonds.

Unsaturated alkyl groups include, without limitation, unsaturated straight-chain, branched or cycloalkyl groups. Unsaturated alkyl groups include without limitation: vinyl, allyl, propenyl, isopropenyl, butenyl, pentenyl, hexenyl, hexadienyl, heptenyl, cyclopropenyl, cyclobutenyl, cyclopentenyl, cyclopentadienyl, cyclohexenyl, cyclohexadienly, 1-propenyl, 2-butenyl, 2-methyl-2-butenyl, ethynyl, propargyl, 3-methyl-1-pentynyl, and 2-heptynyl. Unsaturated alkyl groups can optionally be substituted.

Substitution of alkyl, cycloalkyl and unsaturated alkyl groups includes substitution at one or more carbons in the group by moieties containing heteroatoms. Suitable substituents for these groups include but are not limited to OH, SH, $NH_2$, COH, $CO_2H$, $OR_c$, $SR_c$, $NR_cR_d$, $CONR_cR_d$, and halogens, particularly fluorines where $R_c$ and $R_d$, independently, are alkyl, unsaturated alkyl or aryl groups. Preferred alkyl and unsaturated alkyl groups are lower alkyl, alkenyl or alkynyl groups having from 1 to about 3 carbon atoms.

The term "aryl" is used herein generally to refer to aromatic groups which have at least one ring having a conjugated pi electron system and includes without limitation carbocyclic aryl, aralkyl, heterocyclic aryl, biaryl groups and heterocyclic biaryl, all of which can be optionally substituted. Preferred aryl groups have one or two aromatic rings.

"Carbocyclic aryl" refers to aryl groups in which the aromatic ring atoms are all carbons and includes without limitation phenyl, biphenyl and napthalene groups.

"Aralkyl" refers to an alkyl group substituted with an aryl group. Suitable aralkyl groups include among others benzyl, phenethyl and picolyl, and may be optionally substituted. Aralkyl groups include those with heterocyclic and carbocyclic aromatic moieties.

"Heterocyclic aryl groups" refers to groups having at least one heterocyclic aromatic ring with from 1 to 3 heteroatoms in the ring, the remainder being carbon atoms. Suitable heteroatoms include without limitation oxygen, sulfur, and nitrogen. Heterocyclic aryl groups include among others turanyl, thienyl, pyridyl, pyrrolyl, N-alkyl pyrrolo, pyrimidyl, pyrazinyl, imidazolyl, benzofuiranyl, quinolinyl, and indolyl, all optionally substituted.

"Heterocyclic biaryl" refers to heterocyclic aryls in which a phenyl group is substituted by a heterocyclic aryl group ortho, meta or para to the point of attachment of the phenyl ring to the decalin or cyclohexane. Para substitution is preferred. Heterocyclic biaryl includes among others groups which have a phenyl group substituted with a heterocyclic aromatic ring. The aromatic rings in the heterocyclic biaryl group can be optionally substituted.

"Biaryl" refers to carbocyclic aryl groups in which a phenyl group is substituted by a carbocyclic aryl group ortho, meta or para to the point of attachment of the phenyl ring to the decalin or cyclohexane. Biaryl groups include among others a first phenyl group substituted with a second phenyl ring ortho, meta or para to the point of attachment of the first phenyl ring to the decalin or cyclohexane structure. Para substitution is preferred. The aromatic rings in the biaryl group can be optionally substituted.

Aryl group substitution includes substitutions by non-aryl groups (excluding H) at one or more carbons or where possible at one or more heteroatoms in aromatic rings in the aryl group. Unsubstituted aryl, in contrast, refers to aryl groups in which the aromatic ring carbons are all substituted with H, e.g. unsubstituted phenyl ($-C_6H_5$), or napthyl ($-C_{10}H_7$). Suitable substituents for aryl groups include among others alkyl groups, unsaturated alkyl groups, halogens, OH, SH, $NH_2$, COH, $CO_2H$, $OR_e$, $SR_e$, $NR_eR_f$, $CONR_eR_f$, where $R_e$ and $R_f$ independently are alkyl, unsaturated alkyl or aryl groups. Preferred substituents are OH, SH, $OR_e$, and $SR_e$ where $R_e$ is a lower alkyl, i.e. an alkyl group having from 1 to about 3 carbon atoms. Other preferred substituents are halogens, more preferably fluorine, and lower alkyl and unsaturated lower alkyl groups having from 1 to about 3 carbon atoms. Substituents include bridging groups between aromatic rings in the aryl group, such as $-CO_2-$, $-CO-$, $-O-$, $-S-$, $-NH-$, $-CH=CH-$ and $-(CH_2)_l-$ where l is an integer from 1 to about 5, and particularly $-CH_2-$. Examples of aryl groups having bridging substituents include phenylbenzoate, Substituents also include moieties, such as $-(CH_2)_l-$, $-O-(CH_2)_l-$ or $-OCO-(CH_2)_l-$, where l is an integer from about 2 to 7, as appropriate for the moiety, which bridge two ring atoms in a single aromatic ring as, for example, in a 1, 2, 3, 4-tetrahydronaphthalene group. Alkyl and unsaturated alkyl substitutents of aryl groups can in turn optionally be substituted as described supra for substituted alkyl and unsaturated alkyl groups.

The terms "alkoxy group" and "thioalkoxy group" (also known as mercaptide groups, the sulfur analog of alkoxy groups) take their generally accepted meaning. Alkoxy groups include but are not limited to methoxy, ethoxy, n-propoxy, isopropoxy, n-butoxy, sec-butoxy, isobutoxy, tert-butoxy, n-pentyloxy, neopentyloxy, 2-methylbutoxy, 1-methylbutoxy, 1-ethylpropoxy, 1,1-dimethylpropoxy, n-hexyloxy, 1-methylpentyloxy, 2-methylpentyloxy, 3-methylpentyloxy, 4-methylpentyloxy, 3,3-dimethylbutoxy, 2,2-dimethoxybutoxy, 1-1-dimethylbutoxy, 2-ethylbutoxy, 1-ethylbutoxy, 1,3-dimethylbutoxy, n-pentyloxy, 5-methylhexyloxy, 4-methylhexyloxy, 3-methylhexyloxy, 2-methylhexyloxy, 1-methylhexyloxy, 3-ethylpentyloxy, 2-ethylpentyloxy, 1-ethylpentyloxy, 4,4-dimethylpentyloxy, 3,3-dimethylpentyloxy, 2,2-dimethylpentyloxy, 1,1-dimethylpentyloxy, n-octyloxy, 6-methylheptyloxy, 5-methylheptyloxy, 4-methylheptyloxy, 3-methylheptyloxy, 2-methylheptyloxy, 1-methylheptyloxy, 1-ethylhexyloxy, 1-propylpentyloxy, 3-ethylhexyloxy, 5,5-dimethylhexyloxy, 4,4-dimethylhexyloxy, 2,2-diethylbutoxy, 3,3-diethylbutoxy, 1-methyl-1-propylbutoxy, ethoxymethyl, n-propoxymethyl, isopropoxymethyl, sec-butoxymethyl, isobutoxymethyl, (1-ethylpropoxy)methyl, (2-ethylbutoxy)methyl, (1-ethylbutoxy)methyl, (2-ethylpentyloxy)methyl, (3-ethylpentyloxy)methyl, 2-methoxyethyl, 1-methoxyethyl, 2-ethoxyethyl, 3-methoxypropyl, 2-methoxypropyl, 1-methoxypropyl, 2-ethoxypropyl, 3-(n-propoxy)propyl, 4-methoxybutyl, 2-methoxybutyl, 4-ethoxybutyl, 2-ethoxybutyl, 5-ethoxypentyl, and 6-ethoxyhexyl. Thioalkoxy groups include but are not limited to the sulfur analogs of the alkoxy groups specifically listed supra.

Synthetic Methods

In Schemes 1 and 2, the following text describing the schemes and in the examples, nomenclature, abbreviations and acronyms that are standard and/or well known in the art are employed. More specifically, the meanings of certain terms are as follows: Me, Et, iPr, nBu, tBu, Ph are methyl, ethyl, isopropyl, n-butyl, t-butyl, and phenyl groups, respectively; OAc is an acetate group; EtOAc is ethyl acetate; DMSO is dimethylsulfoxide; DMF is dimethylformamide; THF is tetrahydrofuran; HMPA is hexamethylphosphoramide; MVK is methylvinylketone; TMSCl is trimethylsilyl chloride; LDA is lithium diisopropyl amide; MOM is the methoxymethyl- protecting group.

The synthesis of compounds of formula I is illustrated in Schemes 1 and 2. Scheme 1 exemplifies the synthesis of benzyl-substituted decalins and octalones of formula III where n is 1. Scheme 2 exemplifies a variation of the synthesis of Scheme 1 adapted for phenylethyl-substituted decalins and octalones of formula III where n is 2. The method of Scheme 2 can be employed for those compounds of formula III where n is 2 or more.

In illustrative Scheme 1, the ketodiester 1 is cyclized to give the cyclic ketoester 2 which in turn is reacted with a vinyl ketone, e.g. methyl vinyl ketone (MVK), by sequential Michael addition and Robinson annelation to give an octalone carboxylic acid ester (See: Marshall et al. (1970) *Tetrahedron Lett.*, pp.1239 and Dreiding et al. (1955) *J. Am. Chem. Soc.* 77:411). This ester is decarboxymethylated to give octalone 3 using well-known techniques, for example by nucleophilic decarboxymethylation with alkaline earth salts as described in Tsuda Y. and Sakai Y. (1981) *Synthesis* 119–120 or by hydrolysis and decarboxylation, e.g., with aqueous KOH as described in Oritani et al. (1984) *J. Org. Chem.* 49:3689–3694. See also, McMurry et al. (1976) *Org. React.* 24:188.

More specifically, ketodiester 1 can be obtained by well-known techniques, for example by acid promoted ring opening and subsequent Fischer esterification of furylacrylic acid:

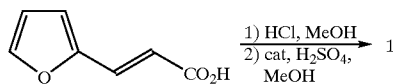

Alternatively, 1 can be prepared by Fischer esterification of 4-ketopimelic acid. The cyclic ketoester 2 can, for example, be formed by reaction of 1 with methyl triphenylphosphonium bromide in NaH/DMSO.

Cyclic ketoester 2 can be converted to octalone 3 by addition to MVK promoted by Triton B or tetrabutylammonium hydroxide followed by annelation using NaOMe/MeOH to give an octalone ester intermediate which is then decarbomethoxylated with $CaCl_2$ —$2H_2O$ in DMSO or LiI —$3H_2O$ in DMF:

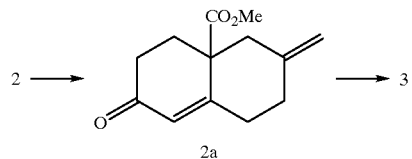

The $Y(CH_2)_n$— group where n is 1, i.e. a substituted benzyl group, is introduced at the C-1 position in octalone 3, by reductive Birch alkylation using lithium in liquid ammonia, for example, using an appropriately protected substituted benzyl group with a good leaving group, such as a chloride, iodide, bromide, methanesulfonate, or p-toluenesulfonate. In Scheme 1, a protected benzyl bromide, 4-MOMO—$C_6H_6$—$CH_2$—Br, (4-MOMO—$C_6H_6$—$CH_2$— is Ar in Scheme 1) is employed. For the specific reaction illustrated in Scheme 1, the yield of alkylated product 4 was low when the protected hydroxybenzyl chloride (4-MOMO—$C_6H_6$—$CH_2$—Cl) was used as the alkylating agent. Protecting groups other than the MOM-group can be employed in the reactions of Scheme 1.

In the illustrated synthesis of Scheme 1, octalone 4 was obtained with the desired α-orientation of the added alkyl group. If a mixture of α- and β-alkylated products are obtained in the alkylation step, the desired α-product can be made by equilibrating the alkylated product in base, such as KOH, NaOMe, or KOtBu, to give the more stable, equatorial α-alkylation product.

Octalone 4 is converted to enone 5 with double bond at the 3,4 position by treatment with lithium diisopropylamide (LDA) or similar non-nucleophilic strong base and reacted with chlorotrimethylsilane (TMSCl), or a similar silane, to form an intermediate silyl enol ether which is dehydrosilylated with palladium(II) acetate [$Pd(OAc)_2$] to give 5. See, Ito et al. (1978) *J. Org. Chem.* 43:1011–1013. Conjugate addition of vinyl magnesium bromide or vinyl lithium using Cu(I) reagents converts enone 5 to the corresponding C-4 substituted vinyl compound, which in turn was alkylated with an alkyl iodoacetate to give the ketoester 6. Specifically, in the illustrated scheme, ethyl iodoacetate is used to give the ethyl ketoester.

Ketoester 6 was converted to the corresponding carboxylic acid which in turn was converted to amide 7. Kinetic hydroboration of the exo-methylene group of 7, followed by reaction with peroxide in the presence of base yields $CH_2OH$ group at C-7 which can be protected, if desired, by reaction with benzylch (oromethyl ether. See, Kende and Roth (1982) *Tet. Letts.* 12:1751–1754. Kinetic hydroboration can be accomplished using catechol borane. Hydroboration of the amide (7) with catechol borane in the presence of Wilkinson's catalyst, followed by work-up with basic peroxide can result in the diol 8. As indicated in Scheme 1, the diol was obtained as a mixture (60/40) of isomers at C-6. The major epimer is the axial carbinol (8a); the minor epimer is the equatorial carbinol (8b). The diol isomers 8a and 8b were separable by flash chromatography. The diol isomer mixture or the individual separated diols can be deprotected, using conventional deprotecting agents, to give the deprotected triol isomer mixture (9) or individual triols 9a and 9b.

Compounds of formula III where W is $CH_2OH$ or $CH_2$ can be prepared from the ketone analogs (where W is CO) by conventional reduction reactions. For example, in Scheme 1 compounds of formula 10 (or the 10a and 10b isomers separately) can be obtained by reduction of the ketone group of the protected amides 8 (or 8a and 8b isomers separately) using metal borohydride reagents.

Compounds of formula XI and XIA where QCO is $EtCO_2$, e.g. compound 11, can be prepared as indicated in Scheme 1 by hydroboration of intermediate 6 using excess catechol borane, as noted above, followed by deprotection (or diol isomer separation followed by deprotection). Compounds 11, 11a or 11b can be fully or partially reduced at C-2 to give analogous compounds of Formula I where W=CHOH or $CH_2$.

Scheme 2 illustrates an alternative to the synthesis of Scheme I to introduce $Y(CH_2)_n$ groups, where n is 2 or more, onto the decalin ring. The synthesis illustrated is for substituted phenylethyl groups (n=2). The Michael acceptor of Scheme 1 (MVK) is replaced with an appropriately aryl-substituted vinyl ketone 22 to introduce the aryl substitutent at C-1. Variation of structure of the $Y(CHe_2)_n$ group is introduced by choice of starting material in this step. β-Ketoester 2 (of Scheme 1) is reacted with the aryl-substituted vinyl ketone 21 to give the cyclic octalone 23. See: Oikawa et al. (1975) *Chem. Pharm. Bull.* 23:2466–2467. Any potentially reactive substitutents of the Y group, such as OH groups, can be protected as indicated in Scheme 2.

Aryl-substituted vinyl ketones, such as 22, can be synthesized from known or readily available starting materials using well-known methods. For example, compound 22 (6-(4-alkoxyphenyl)-1-hexen-3-one can be prepared as indicated in Scheme 2 from readily available starting materials.

The ring double bond of octalone 23 is reduced by Birch reduction followed by enolate equilibration to give the C-1 substituted octalone. The preferred reduction gives the isomer indicated in formula 24, which corresponds to octalone 4 of Scheme 1. The remaining steps of Scheme 2 are substantially as in Scheme 1 and result, for example, in compounds 29a, 29b, 30 and 31.

To obtain compounds of formula I where W is —$CH_2$—, the ketone group at C-2 is reduced by any conventional method. Such a method would include Wolff-Kishner reduction, or Caglioti reduction of the tosylhydrazone by a metal hydride reagent. The ketone group is reduced, preferably under mild conditions.

Specific reaction conditions, solvents and purification methods for the steps of Schemes 1 and 2 can be readily selected and routinely applied by those of ordinary skill in the art in view of the teachings provided herein, by reference to the publications cited herein, and in view of what is well-known in the art of organic synthesis and by routine experimentation and optimization. The particular reagents, reaction conditions and the specific order of steps in the synthesis of Scheme 1 and 2 are illustrative. Those of ordinary skill in the art will appreciate that there is a range of choices for reagents, conditions and reaction order that can be used to achieve the desired synthetic results.

It will also be appreciated by those of ordinary skill in the art, that routine, well-known methods of purification can be employed in the reactions of Schemes 1 and 2. These methods can be used to isolate the final product or when necessary or desirable to isolate intermediate products for further reaction toward the final product. Conventional techniques such as recrystalization of solid products or intermediates, column chromatography, preparative thin layer chromatography, high performance liquid chromatograph (HPLC) and for sufficiently volatile products, gas chromatography or fractional distillation using high vacuum (if necessary) can be readily applied when desired or necessary.

Unless otherwise indicated, the methods of preparation disclosed herein result in product distributions which include all possible structural isomers, although it is understood that physiological response may vary according to structure. Several steps in the schemes are indicated to result in stereoselective incorporation of substituents on the decalin ring system. As will be appreciated by those of ordinary skill in the art, less desired isomers can also be formed as by-products in these steps. The product stereochemistry indicated in the steps of the schemes is believed to be the predominant product with the reagents and starting materials indicated. Less preferred isomers can be removed if necessary or desired by routine methods of purification. The stereoselectivity of individual steps may vary with choice of starting material or reaction conditions. It is well within the ordinary skill in the art in view of the descriptions provided herein to optimize reaction conditions for various choices of starting materials to achieve more preferred stereoisomers.

Unless otherwise indicated, the syntheses described herein result in racemic products. It is understood that physiological response to different enantiomers may vary. Racemic mixtures of enantiomers of compounds of this invention will however retain T4 or CD4 binding activity. One enantiomer of a pair of those of the given formula can have enhanced ability to bind T4 or CD4 receptors compared to their respective mirror image isomers. As will be appreciated by those of ordinary skill in the art, a variety of synthetic techniques are available in the art to obtain enantioselective products. Methods of optical resolution and stereoselective synthesis such as those employed in Oritani and Yamashita (1984) J. Org. Chem. 49: 3689–3693, and references cited herein, can be employed with routine adaptation or modification, if necessary, to prepare and isolate desired enantiomers. Configurations of products can be determined as is well-known in the art by use of conventional techniques including ORD. The methods of Oritani and Yamashita supra and those references cited therein are incorporated by reference herein.

Decalin compounds of formula I–XV (including A and B formulas) can be synthesized by methods of Scheme 1 and 2 or by routine modification or adaptation of those methods by choice of starting materials or reagents. Enantiomers of formulas of compounds of this invention can be synthesized by methods of Scheme 1 and 2 combined with well-known methods of optical resolution and stereoselective synthesis.

Various $Z_1$ and $Z_2$ groups of formula I–XV can be introduced into the decalin structures of this invention by routine modifications and adaptations of the methods of Scheme 1 and Scheme 2 and by application of routine synthetic methods to intermediates of Scheme 1. For example, $Z_1$ and $Z_2$ groups which are ethers, SH, thioethers, $NH_2$, or substituted amino groups ($NR_4R_5$) can be introduced by routine methods starting with intermediates having the —$(CH_2)_m$—OH or —$(CH_2)_p$—OH groups at C-4 and C-6, respectively. In synthesis of compounds having various $Z_1$ and $Z_2$ groups, it may be necessary or desirable to employ different protecting groups which can be differentially removed in order to achieve desired functionalization at the C-4 or C-6 substituents. A variety of appropriate protecting groups are known in the art. It will be appreciated that it may be necessary or desirable to employ protecting groups at other sites in the molecule to achieve desired functionalization. The use of protecting groups is well-understood in the art.

Compounds of formula I–XV (including A and/or B formulas) with various Y—$(CH_2)_n$— groups as listed herein can, for example, by routine selection of alkylating agents, which are appropriated protected as necessary, as in the illustrated alkylations of Scheme 1. Compounds of formula I–XV with various Y—$(CH_2)_n$— groups, where n is 2 or more, as listed herein can, be prepared, for example, by routine selection of starting materials and reagent in view of Scheme 2, the teachings herein and what is well-known in the art of organic synthesis.

$R_1$ of formula 3 of this invention can be H, HO, R'O, R'O—$(CH_2)_q$—, R'S—$(CH_2)_q$—, or R'R"N—CO—$(CH_2)_q$—. These variations of $R_1$ can be prepared by routine modifications and adaptations of the methods of Scheme 1 or Scheme 2. Variations of R' and R" can be readily achieved, for example, by routine adaptation of the amide formation reaction in Schemes 1 or 2 prior to final deprotection.

The cyclohexanes and cylohexanones of formula XVI and XVIA can be synthesized without expense of undue experimentation from readily available starting materials using methods well-known in the art of organic synthesis or by routine adaptation of those methods.

Pharmaceutical Composition and Methods of Treatment

Pharmaceutically acceptable acid addition salts are prepared by contacting compounds of formulas I–XI, IA–XIA, XIIA–XVA, XIIB–XVB, XVI and XVIA having appropriate basic groups therein with an acid whose anion is generally considered suitable for human consumption. Pharmacologically acceptable acid addition salts include but are not limited to the hydrochloride, hydrobromide, hydroiodide, sulfate, phosphate, acetate, propionate, lactate, maleate, malate, succinate, and tartrate salts. All of these salts can be prepared by conventional means by reacting, for example, the selected acid with the selected compound of formula I–XVI.

Pharmaceutically acceptable esters of compounds of formulas I–XI, IA–XIA, XIIA–XVA, XIIB–XVB, XVI and XVIA are prepared by conventional methods, for example by reaction with selected acids. Pharmaceutically acceptable esters include but are not limited to carboxylic acid esters RCOO—D (where D is the cationic form of compounds I–XVI, where R is H, alkyl or aryl groups.

The decalins and octalones of formulas I–XI, IA–XIA, XIIA–XVA, and XIIB–XVB and the cyclohexanes and cyclohexanones of formulas XVI and XVIA have been designed to mimic the three-dimensional structure of peptide T and function in treatment of symptoms of HIV infection by binding T4 receptor and inhibiting binding of HIV. In contrast to peptide T and related peptides that bind to CD4, the peptidomimetics of this invention have significantly longer half-life making them more effective for treatment. Peptidomimetics of this invention will have half-lives in vivo greater than about 60 min. and most typically significantly greater, at least 2-fold higher, than peptide T and related peptides that bind to CD4 under similar in vivo conditions. Most preferred are those compounds of this invention, particularly those of formula I, with half-lives of 24–48 hrs or more.

The relative affinities of different peptides and peptidomimetics for the CD4 receptor can be conveniently monitored using the monocyte chemotaxis assay. Monocytes isolated from the peripheral blood of normal human donors migrate towards a chemical stimulus. The migration phenomenon depends on the interaction of the chemical stimulus with surface receptors on the monocytes. The higher the affinity of an agent for a receptor, the farther the monocytes migrate towards the agent in a given time period. The monocyte chemotaxis assay is described in Example 2.

For peptidomimetics of formula I and XVI having affinity constants for T4 or CD4 receptor substantially similar to that of peptide T for gp120 binding, a dosage of 0.33–0.0003 mg/kg per day is appropriate for treatment. A daily dosage sufficient to achieve a blood concentration of inhibitor of $10^{-6}$ to $10_{-11}$ molar is appropriate for treatment. Appropriate human dosage levels can be readily determined by routine experimentation, for example, in primates. Primates generally require 10 times the dose used in humans.

Preferred compounds of this invention are those having affinity constants for T4 or CD4 receptors of 100 $\mu$molar or greater. More preferred compounds of this invention are those with T4 or CD4 affinity constants of 1 nanomolar or greater.

The CD4 binding compounds of the present invention which inhibit gp120 binding to T4 or CD4 receptor can be used as follows, without limitation, for (a) the treatment or prophylaxis of diseases caused by HIV I, HIV II, and HIV III infections such as AIDS, and stage variations of AIDS such as AIDS related complex, and the suppressed immune response and encephalopathy caused by HIV;

(b) for the treatment and prophylaxis of an HTLV I or HTLV II infection;

(c) for the treatment and prophylaxis of the AIDS carrier or transmitter states; and (d) for the treatment or prophylaxis of infections and diseases caused by retroviruses.

The present invention encompasses pharmaceutical formulations which, in addition to non-toxic, inert pharmaceutically suitable excipients, contain one or more of the compounds of the invention.

Pharmaceutical compositions according to the present invention comprise one or more peptidomimetics of this invention in association with a pharmaceutically acceptable carrier or excipient, adapted for use in human or veterinary medicine. Such compositions may be prepared for use in conventional manner in admixture with one or more physiologically acceptable carriers or excipients. The compositions may optionally further contain one or more other therapeutic agents which may, if desired, be a different antiviral agent.

Thus, the peptidomimetics according to the invention may be formulated for oral, buccal, parenteral, topical or rectal administration. In particular, the peptidomimetics according to the invention may be formulated for injection or for infusion and may be presented in unit dose form in ampules or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g. sterile, pyrogen-free water, before use.

The pharmaceutical compositions according to the invention may also contain other active ingredients such as antimicrobial agents, or preservatives.

In general, pharmaceutical compositions of this invention can contain from 0.001–99% (by weight) of one or more of the compounds of formula I, XVI or XVIA.

The invention further provides a process for preparing a pharmaceutical composition which comprises bringing a peptidomimetic of the invention into association with a pharmaceutically acceptable excipient or carrier.

For administration by injection or infusion, the daily dosage as employed for treatment of an adult human of approximately 70 kg body weight will range from 0.2 mg to 10 mg, preferably 0.5 to 5 mg, which can be administered in 1 to 4 doses, for example, depending on the route of administration and the clinical condition of the patient. These formulations also include formulations in dosage units. This means that the formulations are present in the form of a discrete pharmaceutical unit, for example, as tablets, dragees, capsules, caplets, pills, suppositories or ampules. The active compound content of each unit is a fraction or a multiple of an individual dose. The dosage units can contain, for example, 1, 2, 3 or 4 individual doses for ½, ⅓ or ¼ of an individual dose. An individual dose preferably contains the amount of active compound which is given in one administration and which usually corresponds to a whole, one half, one third or one quarter of a daily dose.

The magnitude of a prophylactic or therapeutic dose of a particular compound will, of course, vary with the nature of the severity of the condition to be treated, the particular compound of Formulas I–XVI and its route of administration. It will also vary according to the age, weight and response of the individual patient.

The compounds of the present invention are preferably formulated prior to administration. The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. The compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 0.5 to about 150 mg, more usually about 0.1 to about 10 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

As a pH adjusting reagent for preparing the pharmaceutical composition, any allowed for preparing medicines can be used, including but not limited to hydrochloric acid-sodium hydroxide, acetic acid-sodium acetate, glycine-sodium chloride-hydrochloric acid, potassium dihydrogenphosphate-disodium hydrogenphosphate, potassium hydrogenphthalate-sodium hydroxide, sodium secondary citrate-hydrochloric acid, sodium dihydrogenphosphate-disodium hydrogenphosphate, sodium dihydrogenphosphate-dipotassium hydrogen-phosphate, potassium dihydrogenphosphate-dipotassium hydrogenphosphate, tartaric acid-sodium tartrate, lactic acid-sodium lactate, sodium barbital-sodium acetate-hydrochloric acid, succinic acid-boric acid, potassium primary citrate-sodium hydroxide, sodium primary citrate-borax, disodium hydrogenphosphate-citric acid, sodium acetate-hydrochloric acid, glutamic acid-sodium hydroxide, and aspartic acid-sodium hydroxide. Among them, hydrochloric acid-sodium hydroxide, acetic acid-sodium acetate, glycine-sodium chloride-hydrochloric acid, tartaric acid-sodium tartrate, lactic acid-sodium lactate, sodium acetate-hydrochloric acid, glutamic acid-sodium hydroxide, and aspartic acid-sodium hydroxide.

The present invention is also directed to combinations of the decalin peptidomimetic HIV inhibitor compounds with one or more other agents useful in the treatment of AIDS. For example, the compounds of this invention may be effectively administered, whether at periods of pre-exposure and/or post-exposure, in combination with effective amounts of the AIDS antivirals, immunomodulators, anti-infectives, or vaccines of Table 1.

It will be understood that the scope of combinations of the compounds of this invention with AIDS antivirals, immunomodulators, anti-infectives or vaccines is not limited to the list in Table 1, but includes in principle any combination with any pharmaceutical composition useful for the treatment of AIDS.

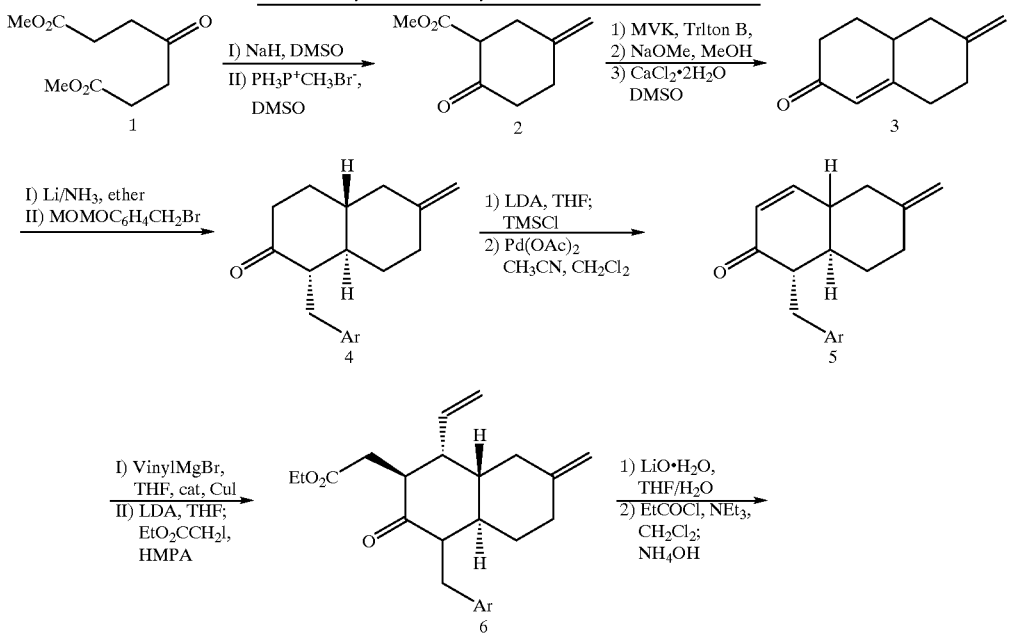

Scheme 1: Synthesis of Benzyl-Substituted Octalones and Decalins

-continued
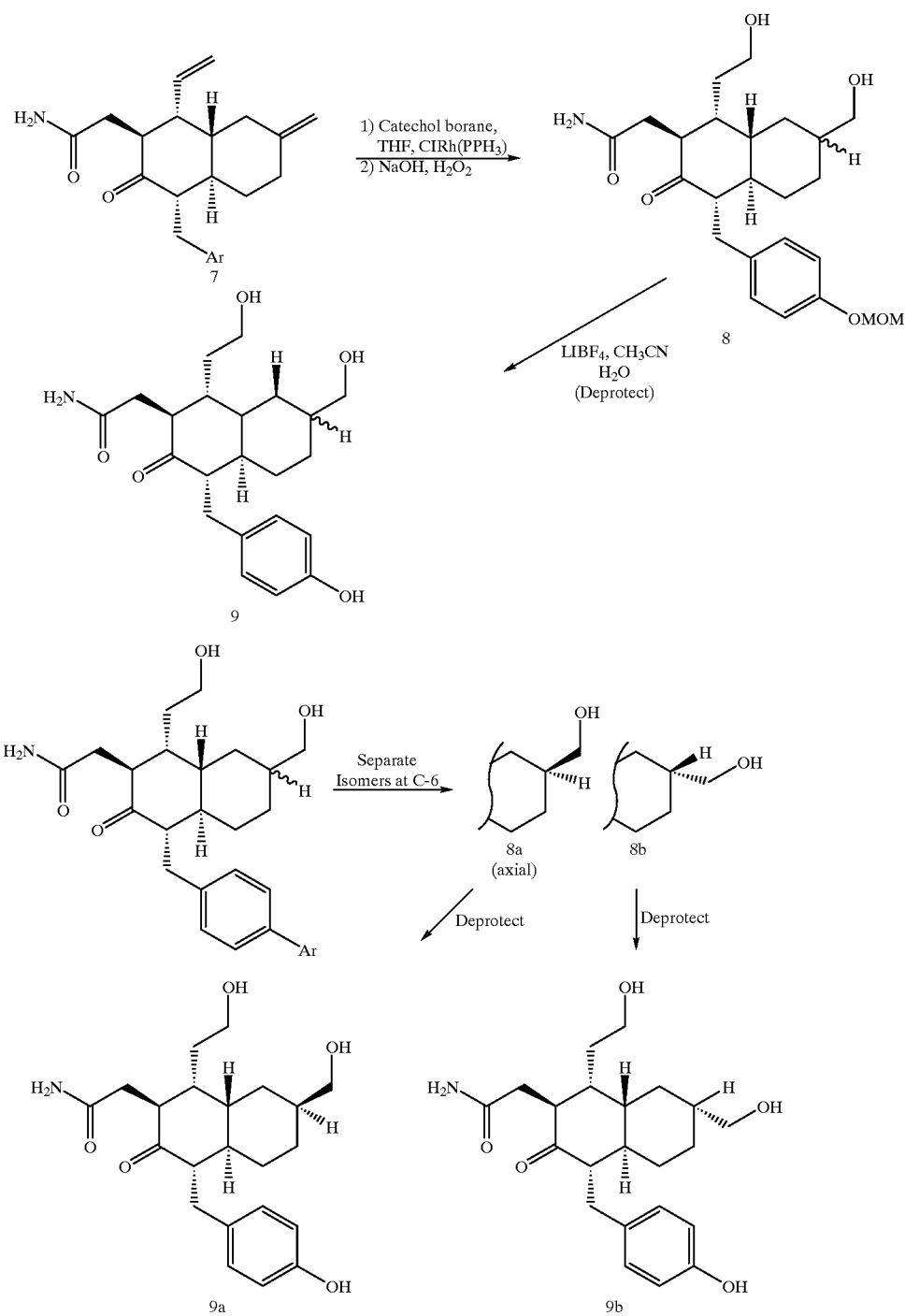

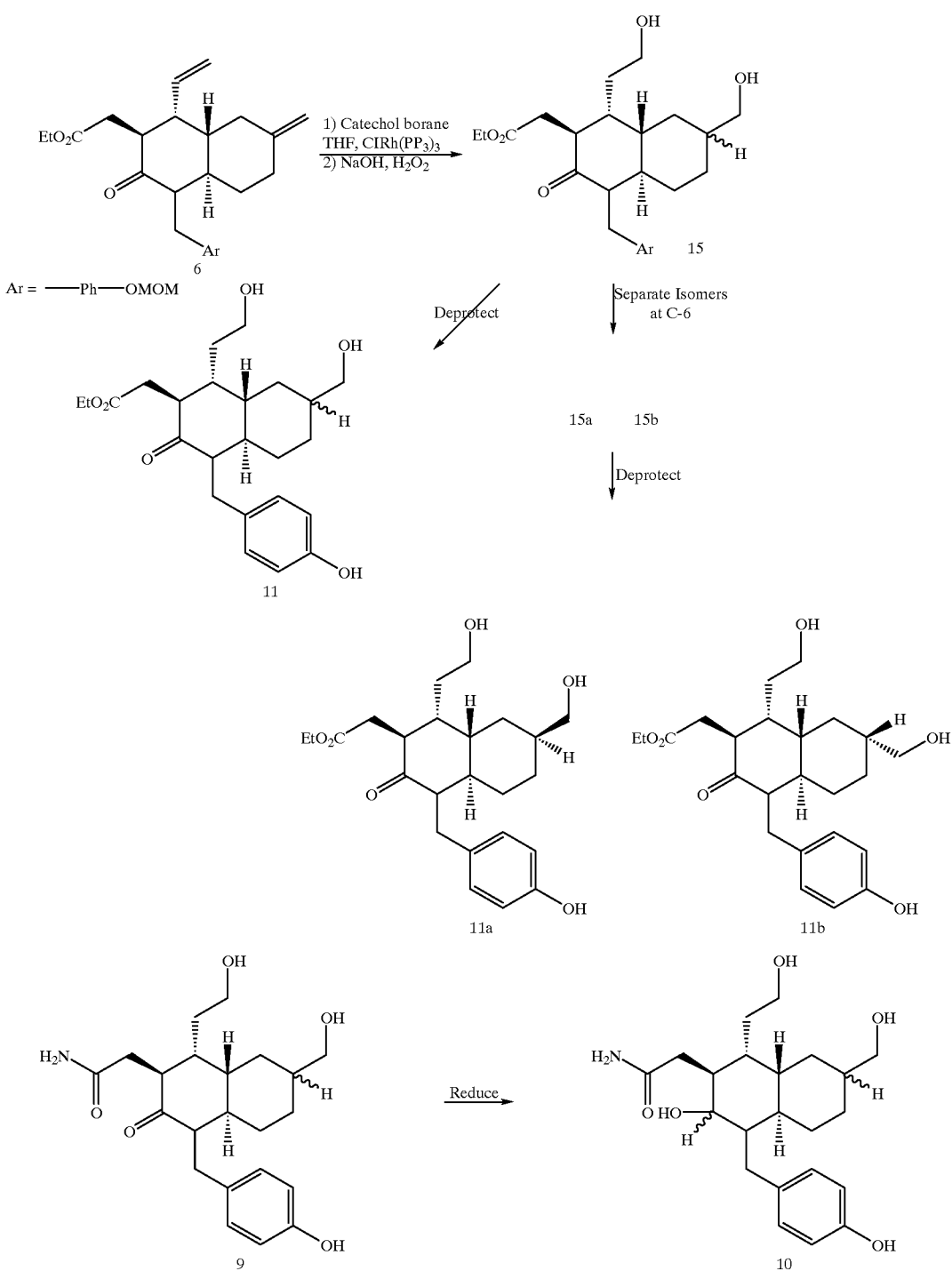

25
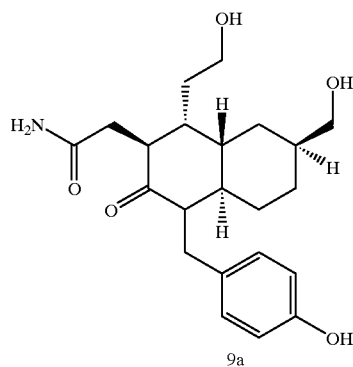
9a
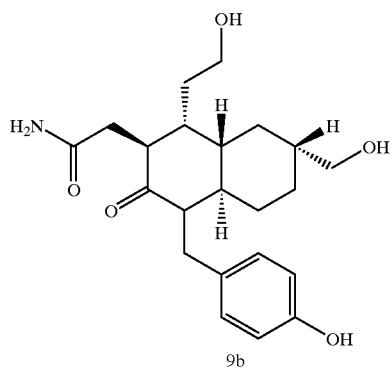
9b
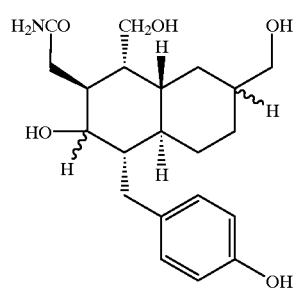
30
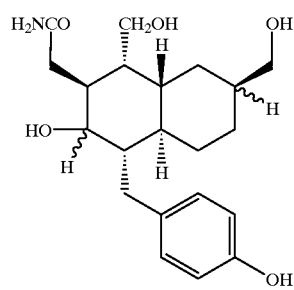
30a
26
-continued
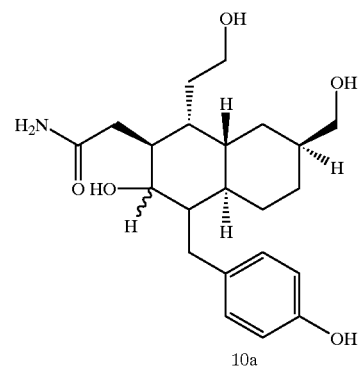
10a
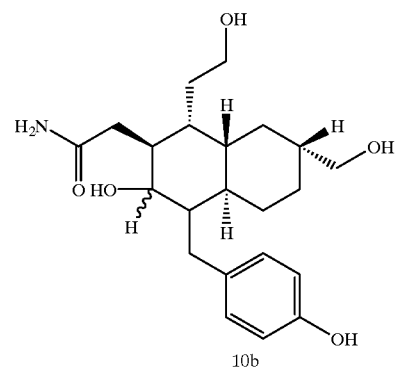
10b
-continued
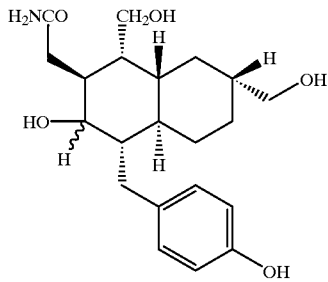
30b
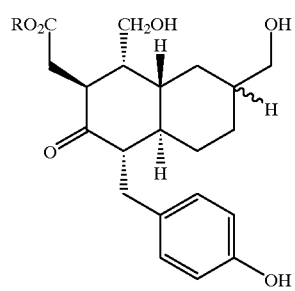
31

-continued

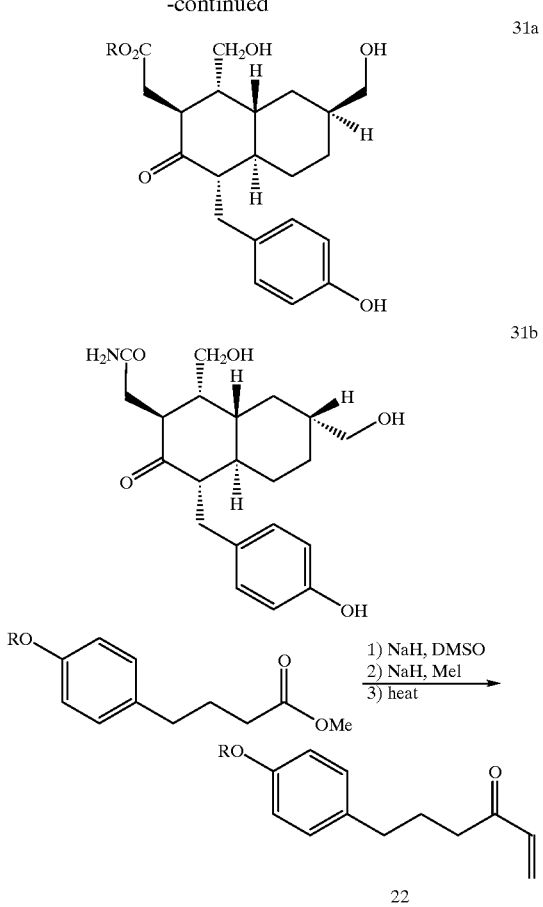

EXAMPLES

Example 1

Exemplary Synthesis of Decalins
Dimethyl-4-ketopimelate (1) by reference to Scheme 1

A three-neck flask equipped with a mechanical stirrer, gas inlet tube and a condenser with a CaCl$_2$ drying tube attached was charged with furylacrylic acid (50 g, 362 mmol) and absolute methanol (200 mL). The solution was stirred vigorously and anhydrous HCl gas was introduced at a rate such that reflux occurred. The flow of HCl was maintained to allow gentle reflux aided by an oil bath at 70° C. The reaction mixture was stirred at reflux for 4 h; the mixture was cooled and the solvent distilled off under reduced pressure. Benzene (150 mL) was then added and the solvent removed at atmospheric pressure until the boiling point of benzene was reached. The remaining solvent was then remove under reduced pressure. The residue was digested with absolute methanol (100 mL); conc. H$_2$SO$_4$ (0.2 mL) was added; and the reaction mixture refluxed for 16 h. Most of the solvent was then distilled off under reduced pressure. The pot residue was dissolved in ether (200 ml) and poured into 1M Na$_2$CO$_3$ (200 mL). The layers were separated and the organic layer washed once with 1M Na$_2$CO$_3$ (200 mL) followed by washing with water (200 mL). The organic layer was then dried over Na$_2$SO$_4$, filtered, concentrated and vacuum distilled to give diester 1.

2-Carbomethoxy-4-methylenecyclohexanone (2)

NaH in dry DMSO (25 mL) was prepared by washing a 60% dispersion of NaH in mineral oil (5.60 g) with pentane (3×) in a stream of Ar. The NaH/DMSO mixture was stirred for 1 h at 75° C. until gas evolution stopped. After the mixture cooled, methyltriphenylphosphonium bromide (50.00, 140 mmol) in 150 mL of dry DMSO was added over about 25 min. The reaction was stirred at room temperature for 1 h and diester 1 (10 g, 54 mmol, in 10 ml dry DMSO) was added. The reaction was stirred at room temperature for 5 h, then acidified to pH 4–5 with glacial acetic acid. The quenched reaction was poured into pentane, and the layers separated. The DMSO layer was extracted with pentane (2×). The combined pentane layers were washed with water (5×), treated with charcoal, dried over MgSO$_4$, and filtered through a pad of Celite. Pentane was removed to give a crude product (2) which was used without further purification.

10-Carbomethoxy-6-methylene-Δ$^{1,9}$-2-octalone

A mixture of ester 2 (4.93 g, 29 mmol) and 170 mL of Triton B (Trademark, Union Carbide Chemicals and Plastics Co., Inc.)(40% (w/v) of benzyltrimethylammonium hydroxide in MeOH) were cooled in an ice-water bath and stirred under Ar. Methyl vinyl ketone (3.2 mL, 28 mmol) was added over 15 min; the resulting reaction mixture was stirred at room temperature for 18 h and diluted with ether. The ether solution was then washed sequentially with water, 1M HCl, sat. NaHCO$_3$, and brine. The washed organic layer was dried over MgSO4, filtered, and concentrated to give the crude Michael adduct as a viscous oil. This addition product was dissolved in anhydrous MeOH (16 mL) and treated with NaOMe (693 mg, 30 mmol Na metal in 18 mL of anhydrous MeOH). The quenched reaction was diluted with ether, washed sequentially with brine, sat. NaHCO$_3$ (saved) and brine. The washed organic layer was dried over MgSO$_4$, filtered and concentrated to give a viscous, yellow oil. The crude material was flash chromatographed on silica gel with hexanes/EtOAc (3:1, v:v) to give a the desired ester as a light yellow solid. The NaHCO$_3$ wash was acidified and extracted with ether. The ether was removed after drying to give a crude by product believed to be the corresponding carboxylic acid.

6-Methylene-Δ$^{1,9}$-2-octalone (3)

The ester, 10-Carbomethoxy-6-methylene-Δ$^{1,9}$-2-octalone, (106 mg, 0.48 mmol) was combined with CaCl$_2$.2H$_2$O (359 mg, 2.4 mmol) in dry DMSO (530 mL) under Ar. The mixture was heated at 145° C. with efficient stirring until the starting material was consumed as indicated by TLC (about 15 h). The reaction was acidified with 1M HCl (about 3 drops, checked with pH paper), cooled to room temperature and diluted with water. The quenched reaction mixture was poured into ether and the layers were separated. The aqueous layer was extracted twice with ether. The ether extracts were combined, washed sequentially with water (3×) and brine (1×), dried over MgSO$_4$, filtered, and concentrated to give a red-orange oil. The crude material was flash chromatographed on silica using hexanes/EtOAc (17:3) to give the octalone (3) as a yellow oil.

6-Methylene-1-[4-(methyloxy)methoxybenzyl]-2-octalone (4)

A 100-ml 3-neck flask with stir bar and condenser (dry ice/iPrOH) was cooled −78° C. under Ar. Anhydrous ammonia was condensed into the flask until it was about ⅓ full, venting ammonia out a mineral oil bubbler. Octalone 3 (502.55 mg, 3.1 mmol) in 4 mL of dry ether was added to the flask. Under a stream of Ar, with the flask maintained at −78° C., small pieces of freshly cut lithium metal were added until an intense blue patch appeared. The reaction was then stirred at −33° C. for 1 h. When the blue color faded, another piece of lithium was added (at −78° C.) to maintain a persistent blue color. After stirring, the reaction, now at −78° C., was diluted with dry ether (20 mL) and the excess lithium metal was quenched by slow, careful addition of 1,2-dibromoethane until the blue color disappeared and the reaction turned white. A solution of 4-(methyloxy) methoxybenzyl bromide (1.44 g, 6.2 mmol) in 4 mL dry ether was added dropwise to the reaction cooled to −78° C. The reaction mixture was then stirred at −33° C. for 50 min. During this time the reaction changed color to a salmon color. The cold condenser was replaced with a water cooled condenser and the ammonia was allowed to boil off overnight. The reaction was then quenched with a small amount of solid NH$_4$Cl and diluted with water. The quenched reaction mixture was poured into ether and the layers separated. The organic layer was sequentially washed with water and brine, dried over Na$_2$SO$_4$, filtered and concentrated in vacuo to give the crude product as a pale orange viscous oil. The oil was flash chromatographed on silica gel using hexanes/EtOAc (9:1) to give 4 as a solid melting at about 75–77° C. (with apparent sublimation occurring). High resolution MS(E1) for C$_{20}$H$_{26}$O$_3$: cal. 314.1882; found 314.1884.

6-Methylene-1-[4-(methyloxy)methoxybenzyl]-Δ$^{3,4}$-2-octalone (5)

Diisopropylamine (0.27 mL, 1.9 mmol) in dry THF (5.2 mL) was cooled with stirring to 0° C. under Ar. A solution of nBuLi in hexanes (1.6M, 1.1 mL) was then added to the cooled mixture. The reaction was stirred for 20 min (0° C.), then cooled to −78° C. A solution of octalone 4 (493.85 mg, 1.6 mmol) in dry THF (3.8 mL) was added dropwise to the cooled reaction over 17 min. The reaction mixture was stirred at −78° C. for 1 hr, after which neat TMSCl (0.4 mL, 3.2 mmol) was added. The reaction mixture was stirred for an additional 30 min at −78° C., warmed to room temperature and stirred for 90 min. The reaction mixture was then diluted with pentane (to give 100 mL total), and washed quickly with ice-cold sat. NaHCO$_3$ (2×50 mL). The organic layer was dried over Na$_{2SO}$4, filtered, and concentrated to give a quantitative yield of the silyl enol ether analog. The crude silyl enol ether product was dissolved in 1:1 CH$_3$CN/CH$_2$Cl$_2$ (1.6 mL) and added to a solution of Pd(OAc)$_2$ (429.70 mg, 1.9 mmol) in dry CH$_3$CH (7.2 mL) under Ar. The resulting reaction mixture was stirred for 20 h at room temperature, after which the solvents were removed on a rotary evaporator. The residue was stirred with EtOAc briefly, the palladium mirror scraped from the sides of the flask, and the suspension filtered through a pad of Celite. The filtrate was washed sequentially with sat. NaHCO$_3$ (75 mL), water (75 mL) and brine (75 mL). The washed organic layer was dried over Na$_2$SO$_4$, filtered, and concentrated to give a red-orange oil. The crude material was flashed chromatographed on silica gel using Hexanes/EtOAc (17:3) to give desired product enone 5 as a yellow oil.

3-Carboethyoxymethyl-6-methylene-1-[4-(methyloxy)methoxybenzyl]-4-vinyl-2-octalone (6)

Enone 5 (25.2 mg, 0.81 mmol) was combined with Cu(I)iodide 25.37 mg, 0.13 mmol) in dry THF (1.9 mL) under Ar. The resulting suspension was cooled to −78° C. and a solution of vinyl magnesium bromide in THF (1M, 1.6 mL) was added dropwise over 12 min. The reaction was stirred at −78° C. for 20 min, then maintained at −20° C. to −30° C. for 1.5 h. HMPA (140 μL, 0.81 mmol) was then added to the reaction, followed by dropwise addition of neat ethyl iodoacetate (280 μL, 2.4 mmol). The reaction was then stirred at −20° C. for 1 h, warmed to room temperature, and stirred for another 19 h. The reaction was quenched with sat. NH$_4$Cl, diluted with water and ether, and stirred for 20 min until the aqueous layer turned blue. The quenched reaction mixture was poured into ether (30 mL) and the layers separated. The aqueous layer was extracted once with ether (20 mL). The combined ether layers were sequentially washed with water (2×) and brine. The organic layer was dried over Na$_2$SO$_4$, filtered, and concentrated to give crude product 6. The crude material was flash chromatographed on silica gel using hexanes/EtOAc (9:1) to give product the ketoester octalone 6 as a yellow oil.

3-α-Acetamido-6-methylene-1-[4-(methyloxy)methoxybenzyl]-4-vinyl-2-octalone (7).

Ketoester octalone 6 (51.59 mg, 0.12 mmol) was combined with LiOH2H$_2$O (67.38 mg, 1.6 mmol) in THF (0.24 mL) and water (0.06 mL) under Ar. The suspension was stirred at room temperature for 17.5 h, then the reaction mixture was diluted with water and acidified with 0.5N HCl to about pH 3 (solution becomes milky). The mixture was poured into ether and the layers separated. The aqueous layer was extracted once with ether and the ether extracts were combined and washed with brine. The organic layer was dried over NA$_2$SO$_4$, filtered, and concentrated to give the crude carboxylic acid octalone (3-carboxymethyl-6-methylene-1-[4-(methyloxy)methoxybenzyl]-4-vinyl-2-octalone) which was used without further purification. Crude carboxylic acid (43.3 mg, 0.11 mmol) was dissolved in dry CH$_2$Cl$_2$ (0.40 mL) under Ar. Triethyl amine (NEt$_3$, 0.02 mL, 0.13 mmol) followed by ethyl chloroformate (0.012 mL, 0.13 mmol) was added to the cooled (0° C.), stirred reaction mixture. The reaction was then stirred at 0° C. for 30 min., after which 0.03 mL of 30% (wt/vol) NH$_4$OH was added. The reaction was stirred vigorously for 4 h at room temperature, diluted with water, and poured into CHCl$_3$ (25 mL). The layers were separated and the aqueous layer was washed once with CHCl$_3$ (20 mL). The organic extracts were combined, washed once with brine, dried over Na$_2$SO$_4$, filtered and concentrated to give crude amide (7). The crude material was flash chromatographed on deactivated silica using EtOAc/Hexanes (4:1) containing 3% NEt$_3$ to give 7 as a solid.

3-α-Acetamido-4-(2-hydroxyethyl)-6-hydroxymethyl-1-[4-(methyloxy)methoxybenzyl]-2-octalone (8).

Amide (7) (45.1 mg, 0.11 mmol) was combined with Wilkinson's catalyst (11.6 mg, 0.013 mmol) in dry THF (0.5 mL) under Ar. The mixture was stirred at room temperature for several minutes to obtain a homogeneous solution. A solution of catechol borane in THF (1M, 0.33 mL) was added to the reaction mixture which was then stirred at room temperature for 18 h, cooled to 0° C., treated first with 3M NaOH (0.5 mL), followed by 30% H$_2$O$_2$ (0.2 mL) and stirred for another 2 h. The reaction mixture was diluted with water and EtOAc. The quenched reaction was poured into EtOAC (20 mL) and 2M NAOH (20 mL) and the layers were separated. The aqueous layer was extracted once with EtOAc (20 mL), the organic layers combined, washed twice with 2M NaOH (20 mL) and once with brine (25 mL). The organic layer was dried with Na$_2$SO$_4$, filtered, and concentrated to give crude tan-colored residue. The crude material was flash chromatographed on silica using $CH_2Cl_2/MeOH$ (17:1) to elute one of the C-6 isomers, then with $CH_2Cl_2/MeOH$ (7:3) to elute off the second C-6 isomer. The isomers were obtained in a ratio of about 60/40 major isomer (8a) to minor isomer (8b).

3-α-Acetamido-1-(4-hydroxybenzyl)-4-(2-hdyroxyethyl)-6-hydroxymethyl-2-octalone (9).

The major isomer (8a) (125.1 mg, 0.29 mmol) was combined with $LiBF_4$ (140.6 mg, 1.5 mmol) in $CH_3CN$ (1.5 mL) and water (0.30 mL) under Ar and stirred at 80° C. for 4 h. The reaction mixture was cooled to room temperature and quenched by dropwise addition of sat. $NaHCO_3$. The quenched reaction was poured into EtOAc (20 mL) and the layers separated. The aqueous layer was saturated with solid NaCl, and extracted with EtOAc (5×10 mL). The EtOAc extracts were combined, dried over $Na_2SO_4$, filtered and concentrated to give crude amber-colored material. The crude material was flash chromatographed on silica using $CHCl_3/MeOH$ (9:1) to give a vanilla-colored solid (9a).

The minor isomer (8b) (28.8 mg, 0.065 mmol) was combined with $LiBF_4$ (36.6 mg, 0.39 mmol) in $CH_3CN$ (0.28 mL) and water (0.06 mL) under Ar and stirred at 80° C. for 4 h. The reaction was worked up as for the major isomer to give a crude amber-orange solid. The crude material was flash chromatographed on silica using $CHCl_3/MeOH$ (8:1) to give a vanilla-colored solid (9b).

3-α-Acetamido-1-(4-hydroxybenzyl)-2-hydroxy-4-(2-hydroxyethyl)-6-α-hydroxymethyloctalone (10a)

To 6.0 mg of amide (9a) in 0.10 mL absolute ethanol (at 20° C.) is added 2.3 mg of sodium borohydride. The stirred solution is cooled to 0°, held at this temperature for 2 h, allowed to warm to about 25° C. and then stirred for an additional 4 h. The desired product is isolated by aqueous workup and extraction with ethylacetate, followed by drying. Removal of solvent gives a crude product which is chromatographed over a short silica gel column using 3:1 chloroform-methanol to give 5.8 mg of the carbinol 10α as an epimeric mixture at C-2.

3-α-Carboethoxymethyl-4-(2-hydroxyethyl)-6-(hydroxymethyl)-1-(4-hydroxyphenyl)-2-octalone (11)

The protected octalone ester (6a) is reacted with $LiBF_4$ (14.3 mg, 0.15 mmol) in $CH_3CN$ (250 μL) and $H_2O$ (25 μL, 10% v/v) under Ar. The reaction was heated to about 78° C. and stirred under Ar for 5.5 h. The reaction is cooled to RT, then sat. $NaHCO_3$ is added dropwise to quench the reaction. The quenched reaction was diluted with EtOAc and $H_2O$, then poured into EtOAc. The layers were separated and the aqueous layer extracted once with EtOAc. The organic extracts were combined, washed once with brine, dried over $Na_2SO_4$, filtered and concentrated. The crude residue was purified by flash chromatography on silica gel with EtOAc/Hexanes (1:1) to give a first cut, then with 100% EtOAc to give a second cut which contains the purified deprotected ester product.

Example 2

Monocyte Chemotaxis Assay

While normally performed in a chemotaxis chamber, this assay can be performed simply and inexpensively using petri dishes. Agar is poured into a petri dish and three concentric wells are bored into the agar. The potential chemotactic agent is placed in the innermost well, monocytes are placed in the central well, and buffer is placed is the outer well. Monocytes migrate towards the central well under the agar and along the bottom of the dish. At the end of a particular experiment, the agar is removed, and the monocytes are stained. Net migration is computed as the difference between the migration of monocytes towards the central well and the random migration towards the control buffer. A dose-response curve is obtained by plotting net migration as a function of chemotactic agent concentration. For details of the monocyte chemotaxis assay see, Licht, D., Cronstein, B., Dykes, D. C., Pedersen, J., Luster, S. M., Trampota, M., Hull, E., Friedman, F. K., and Pincus, M. R. (1992) J. Protein Chem. 11, 475–481.

Example 3

Inhibition of Replication of HIV Virus in vitro

The peptidomimetics disclosed herein exhibit an inhibitory effect on retroviruses, and in particular, on human immunodeficiency virus (HIV). The median effective concentrations ($EC_{50}$) of selected peptidomimetics against HIV-1 can be determined in human blood mononuclear (PBM) cells infected with HIV-1 (strain LAV).

$EC_{50}$ values for selected compounds can be obtained by the following procedure:

a. Three-day-old phytohemagglutinin-stimulated PBM cells ($10^6$ cells/ml) from hepatitis B and HIV-1 seronegative healthy donors are infected with HIV-1 (strain LAV) at a concentration of about 100 times the 50% tissue culture infectious dose (TICD 50)/ml and cultured in the presence and absence of various concentrations of the test compound;

b. Approximately 45 min after infection, medium containing the test compound (2 times the final concentration in medium) is added to the flasks (5 ml; final volume 10 ml) from step a. Medium controls are also performed. AZT can be employed as a positive control;

c. Cells are then exposed to HIV (about $2.0 \times 10^5$ dpm/ml, as determined by reverse transcriptase assay) and placed in a $CO_2$ incubator. HIV-1 (strain LAV) available from the Center for Disease Control, Atlanta, Ga., can be employed. Methods for culturing the PBM cells, harvesting the virus and determining the reverse transcriptase activity are, for example, those described by McDougal et al. (J. Immun. Meth. 76, 171–183, 1985) and Spira et al. (J. Clin. Meth. 25, 97–99, 1987), except that fungizone was excluded from the medium (see Schinazi, et al., Antimicrob. Agents Chemother. 32, 1784–1787 (1988)). The reverse transcriptase activity in the virus-infected control is suitably about $2 \times 10^5$ dpm/ml. Blank and uninfected cell controls are also performed;

d. On day 6, the cells and media are transferred to a 15 ml tube and sedimented at about 900×g for a 10-min period. An aliquot of supernatant (about 5 ml) is removed and the virus concentrated by centrifugation at 40,000 rpm for 30 minutes (Beckman 70.1 Ti rotor). The solubilized virus pellet is processed for determination of the levels of reverse transcriptase. Results are expressed in dpm/ml of sampled supernatant.

The median effective ($EC_{50}$) concentrations for the compounds of this invention is determined by the median effect method (Antimicrob. Agents Chemother. 30,: 491–498, 1986). Briefly, in the median effect method, the percent inhibition of virus, as determined from measurements of reverse transcriptase, is plotted versus the micromolar concentration of test compound. The $EC_{50}$ is the concentration of compound at which there is a 50% inhibition of viral replication.

Example 4

Binding Competition Assay

The CD4 receptor which has been cloned and over expressed, is now available in purified form for direct binding assays. Binding assays are performed with decalins of this invention using filter binding assays. Assay procedures, as described in Carucci, I. E. et al. (1989) Med. Sci. Res. 17: 559–560, can be employed with appropriate routine adaptation for application to decalins. For filter binding assays, decalins are radiolabeled employing any labeling methods known in the art which can be adapted, as well be understood in the art, for labeling decalins.

Example 5

Pharmaceutical Formulations of Decalins Octalones or Cyclohexanones of Formulas I–XVI, IIIA–XVIA and XIIB–XVB The following formulations are illustrative only and are not intended to limit the scope of the invention in any way. In the following formulations "Active Ingredient" means a decalin, octalone, cyclohexane or, cyclohexanone of this invention of formulas I–XVI, IIIA–XVIA, XIIB–XVB, or mixtures thereof.

FORMULATION 1

Hard gelatin capsules are prepared using the following ingredients, where a

|  | mg/capsule |
| --- | --- |
| Active Ingredient | 0.25 |
| Starch, dried | 425 |
| Magnesium stearate | 10 |

The above ingredients are mixed and filled into hard gelatin capsules.

FORMULATION 2

A tablet formula is prepared using the ingredients below:

|  | mg/tablet |
| --- | --- |
| Active Ingredient | 0.25 |
| Cellulose, microcrystalline | 6.25 |
| Colloidal Silicon Dioxide | 10 |
| Stearic acid | 5 |

The components are blended and compressed to form tablets.

FORMULATION 3

A dry powder inhaler formulation is prepared containing the following components:

|  | Weight % |
| --- | --- |
| Active Ingredient | 1% |
| Lactose | 99% |

The active compound is mixed with the lactose and the mixture added to a dry powder inhaling appliance.

FORMULATION 4

Tablets each containing 0.60 mg of active ingredient are made up as follows:

|  | mg/tablet |
| --- | --- |
| Active Ingredient | 0.60 |
| Starch | 45 |
| Microcrystalline cellulose | 35 |
| Polyvinylpyrrolidone (10% solution in water) | 4 |
| Sodium carboxytmethyl starch | 4.5 |
| Magnesium stearate | 0.5 |
| Talc | 1 |

The active ingredient, starch and cellulose are passed through a No. 20 mesh U.S. sieve and mixed thoroughly. The solution of polyvinylpyrrolidone is mixed with the resultant powders which are then passed through a No. 4 mesh U.S. sieve. The granules so produced are dried at 50° to 60° C. and passed through a No. 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets.

FORMULATION 5

Capsules each containing 2 mg of medicament are made as follows:

|  | mg/capsule |
| --- | --- |
| Active Ingredient | 2 |
| Starch | 169 |
| Magnesium Stearate | 3 |

The active ingredient, cellulose, starch and magnesium stearate are blended, passed through a No. 20 mesh U.S. sieve, and filled into hard gelatin capsules.

FORMULATION 6

Suppositories each containing 25 mg of active ingredient are made as follows:

|  | mg/suppository |
| --- | --- |
| Active Ingredient | 25 |
| Saturated fatty acid glycerides | 2,000 |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 5 mg of medicament per 5 ml dose are made as follows:

|  | mg/5 ml dose |
| --- | --- |
| Active Ingredient | 5 |
| Sucrose | 1,750 |
| Xanthan Gum | 4 |
| Sodium carboxymethyl cellulose (11%) | 50 |
| Sodium benzoate | 10 |
| Flavor | q.v |

-continued

| | mg/5 ml dose |
|---|---|
| Color | q.v |
| Purified water to | 5 ml |

The medicament, sucrose and xanthan gum are blended, passed through a No. 10 mesh U.S. sieve, and then mixed with a previously made solution of the microcrystalline cellulose and sodium carboxymethylcellulose in water. The sodium benzoate, flavor and color are diluted with some of the water and added with stirring. Sufficient water is then added to produce the required volume.

FORMULATION 8

| Solution for Injection I | (50 mg/ml) |
|---|---|
| Active Ingredient | 5.0% w/v |
| 1M Sodium Hydroxide | 15.0% w/v |
| Polyethylene glycol 400 | 4.5% w/v |
| 0.1 M HCl (to adjust pH to 7.6) | |
| Water for injection q.s to 100% | |

FORMULATION 9

| Solution for Injection II | (10 mg/ml) |
|---|---|
| Active Ingredient | 1.0% w/v |
| 0.1 M Sodium Hydroxide | 15.0% w/v |
| Sodium phosphate BP | 3.6% w/v |
| Water for injection q.s to 100% | |

FORMULATION 10

| Solution for Injection III | (1 mg/ml, buffered to pH 6) |
|---|---|
| Active Ingredient | 0.1% w/v |
| Sodium phosphate BP | 2.26% w/v |
| Citric acid | 0.38% w/v |
| Polyethylene glycol 400 | 3.5% w/v |
| Water for injection q.s to 100% | |

The specific embodiments described herein are included only to illustrate the invention. It will be apparent to those of ordinary skill in the art that variations, modifications and adaptations of the specific procedures, methods and expedients described herein can be made without departing from the spirit and scope of this invention.

TABLE 1

| Drug Name | Manufacturer | Indication |
|---|---|---|
| ANTIVIRALS | | |
| AL-721 | Ethigen (Los Angeles, CA) | ARC,PGL, HIV positive, AIDS |
| Recombinant Human Interferon Beta | Triton Biosciences (Alameda, CA) | AIDS, Kaposi's sarcoma, ARC |
| Acemannan | Carrington Labs (Irving, TX) | ARC |
| Cytovene | Syntex (Palo Alto, CA) | sight-threatening CMV |
| Ganciclovir | | peripheral CMV retinitis |
| d4T | Bristol-Meyers (New York, NY) | AIDS, ARC |
| Didehydrodeoxy-thymidine | | AIDS, ARC |
| Dideoxyinosine (ddI) | Bristol-Meyers | AIDS, ARC |
| EL10 | Elan Corp., PLC (Gainesville, GA) | HIV infection |
| Foscarnet | Astra Pharm. | CMV retinitis, HIV |
| Dideoxycytidine (ddC) | Hoffman-la-Roche (Nutley, NJ) | AIDS, ARC |
| Novapren | Novaferon Labs., Inc. (Akron, OH) | HIV inhibitor |
| Peptide T | Peninsular Labs (Belmont, CA) | AIDS |
| Retrovir | Burroughs Wellcome (Rsch. Triangle Park, NC) | AIDS, adv, ARC, pediatric |
| Zidovudine; AZT | | AIDS, Kaposi's sarcoma, asymptomatic HIV infection, less severe HIV disease, neurological involvement, in combination w/other therapies, post exposure prophylaxis in health care workers |
| Rifabutin | Adria Laboratories | ARC |
| Ansamycin LM 427 | Erbamont (Stamford, CT) | ARC |
| Dextran Sulfate | Ueno Fine Chem. Ind. Ltd. (Osaka, Japan) | AIDS, ARC, HIV positive asymptomatic |
| Virazole (Ribavirin) | Viratek/ICN (Costa Mesa, CA) | asymptomatic HIV positive, LAS, ARC |
| Alpha Interferon | Burroughs Wellcome | Kaposi's sarcoma, HIV |

TABLE 1-continued

| Drug Name | Manufacturer | Indication |
|---|---|---|
| | (Rsch. Triangle Park, NC) | |
| IMMUNOMODULATORS | | |
| AS-101 | Wyeth-Ayerst Labs. (Philadelphia, PA) | AIDS |
| Bropirimine | Upjohn | advanced AIDS |
| CL246,738 | American Cyanamid Lederle Labs (Pearl River, NY) | AIDS, Kaposi's sarcoma |
| Gamma Interferon | Genentech (S. San Francisco, CA) | ARC (in combination W/TNF (tumor necrosis factor) |
| Granulocyte Macrophage Colony Stimulating Factor | Various | AIDS |
| IL-2 (Interleukin-2) | Cetus Hoffman-La Roche | AIDS |
| Immune Globulin | Cutter Biological (Berkeley, CA) | pediatric AIDS |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl | Merieux Institute (Miami, FL) | AIDS, ARC |
| Dithio Carbamate | | AIDS, ARC |
| INTRON A, Alpha-2 | Schering Plough (Madison, NJ) | Kaposi's sarcoma w/Retrovir: AIDS |
| Interferon Methionine- Enkephalin | TNI Pharmaceutical (Chicago, IL) | AIDS, ARC |
| MTP-PE | Ciba-Geigy Corp. (Summit, NJ) | Kaposi's sarcoma |
| Muramyl-Tripeptide GranulocyteColony Stimulating Factor | Amgen (Thousand Oaks, CA) | AIDS, in combination w/Retrovir |
| rCD4 Recombinant Soluble Human CD4 rCD4-IgG hybrids | Genentech (S. San Francisco, CA) | AIDS ARC Recombinant |
| Recombinant Soluble Human CD4 | Biogen (Cambridge, MA) | AIDS, ARC |
| Roferon-A Interferon Alfa 2a | Hoffman-La Roche (Nutley, NJ) | Kaposi's sarcoma, AIDS, ARC, in combination w/Retrovir |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Diflucan Fluconazole | Pfizer (New York, NY) | cryptococcal meningitis, candidiasis |
| Pastille Nystatin Pastille | Squibb Corp. (Princeton, NJ) | prevention of oral candidiasis |
| Ornidyl Eflornithine | Merrell Dow (Cincinnati, OH) | PCP treatment |
| Pentamidine Isethionate (IM & IV) | LyphoMed (Rosemont, IL) | PCP treatment |
| Piritrexim | Burroughs Wellcome (Rsch. Triangle Park, NC) | PCP treatment |
| Pentamidine isethionate | Fisons Corporation (Bedford, MA) | PCP prophylaxis for inhalation |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; crypotoccal meningitis |
| Trimetrexate | Warner-Lambert | PCP |
| OTHER | | |
| Recombinant Human Erythropoietin | Ortho Pharm. Corp. (Raritan, NJ) | severe anemia assoc. and Retrovir therapy |

TABLE 1-continued

| Drug Name | Manufacturer | Indication |
|---|---|---|
| Megestrol Acetate | Bristol-Meyers (New York, NY) | treatment of anorexia assoc. w/AIDS |
| Total Enteral | Norwich Eaton Pharmaceuticals (Norwich, NY) | diarrhea and malabsorption related |

It will be understood that the scope of combinations of the compounds of this invention with AIDS antivirals, immunomodulators, anti-infectives or vaccines is not limited to the list in Table 1 above, but includes in principle any combination with any pharmaceutical composition useful for the treatment of AIDS.

We claim:

1. A compound of the formula:

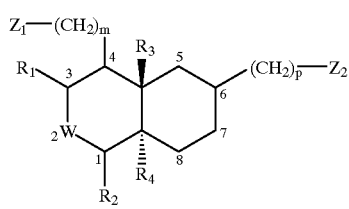

I and enantiomers thereof, wherein:

$R_1$ is selected from the group consisting of a hydrogen, an R' group, HO, R'O group, an R'O—$(CH_2)_q$, or a QCO—$(CH_2)_q$ group, where q an integer from 0 to about 5, and where Q is R', R'O, R'S, or R'R"N;

$Z_1$ and $Z_2$, independently of one another, are $R_5R_6N$, $R_7O$, or $R_8S$ groups and m and p are integers from 1 to about 5;

$R_3$ and $R_4$, independently of one another, are a hydrogen, an alkyl group or an unsaturated alkyl group;

$R_2$ is any hydrocarbyl or substituted hydrocarbyl group; and

W is a $CH_2$, a CH—OH or a C=O group; and wherein substituents R', R" and $R_5$–$R_8$, independently of one another, can be a hydrogen, a hydrocarbyl or substituted hydrocarbyl group.

2. The compound of claim 1 wherein R' and R", independently of one another, can be a hydrogen, an alkyl group, a substituted alkyl group, an unsaturated alkyl group, a substituted unsaturated alkyl group, an aryl group or a substituted aryl group.

3. The compound of claim 1 wherein R' and R", independently of one another, can be a hydrogen or an alkyl group.

4. The compound of claim 1 wherein $R_5$–$R_8$, independently of one another, can be a hydrogen, an alkyl group, or an unsaturated alkyl group.

5. The compound according to claim 1 having the formula:

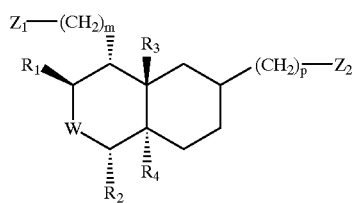

II and enantiomers thereof.

6. The compound according to claim 1 having the formula:

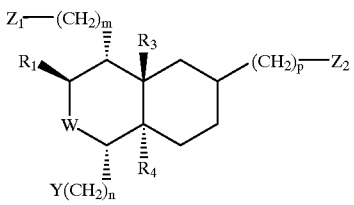

III and enantiomers thereof, wherein Y is an aryl group which can optionally be substituted.

7. The compound according to claim 1 having the formula:

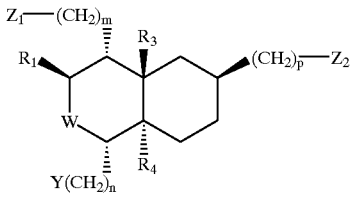

IIIA and enantiomers thereof wherein Y is an aryl group which can optionally be substituted.

8. The compound according to claim 7 wherein $Z_1$ and $Z_2$, independently of one another, are $R_7O$, wherein $R_7$ is a hydrogen or an alkyl group.

9. The compound according to claim 8 wherein $Z_1$ and $Z_2$ are OH groups, and p is an integer from 1 to about 3.

10. The compound according to claim 9 wherein Y is a 4-hydroxyphenyl group and $R_3$ and $R_4$, independently of one another, can be a hydrogen or a methyl group.

11. The compound according to claim 1 having the formula:

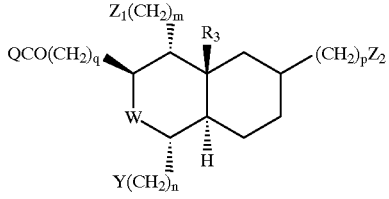

IV and enantiomers thereof.

12. The compound according to claim 1 having the formula:

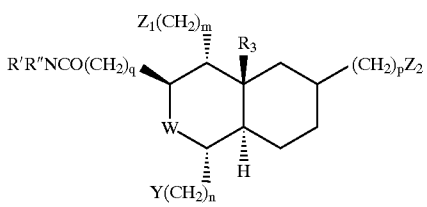

V and enantiomers thereof.

13. The compound according to claim 1 having the formula:

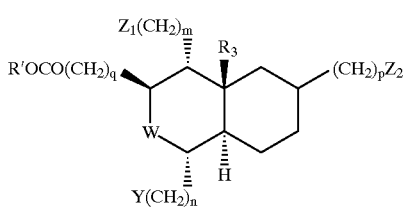

VI and enantiomers thereof.

14. The compound according to claim 1 having the formula:

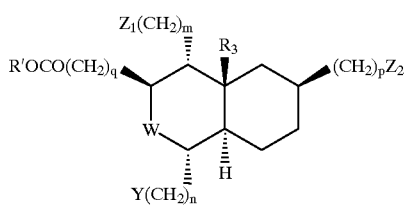

VIA and enantiomers thereof wherein Y is an aryl or substituted aryl group.

15. The compound according to claim 1 having the formula:

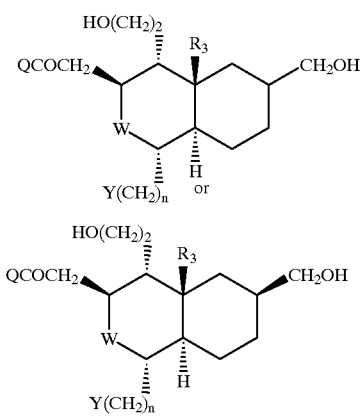

X or

XA and enantiomers thereof.

16. The compound according to claim 1 having the formula:

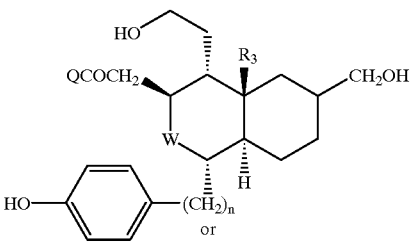

XI or

XIA and enantiomers thereof.

17. The compounds according to claim 15 wherein n is 1 or 2.

18. The compounds according to claim 1 wherein W is —$CH_2$—.

19. The compounds according to claim 1 wherein W is C=O.

20. The compounds according to claim 1 wherein W is CH—OH.

21. The compounds according to claim 1 wherein $Z_1$—$(CH_2)_n$— is selected from the group $H_2NCOCH_2$— or $CH_3CH_2OCOCH_2$—.

22. The compound according to claim 1 having the formula:

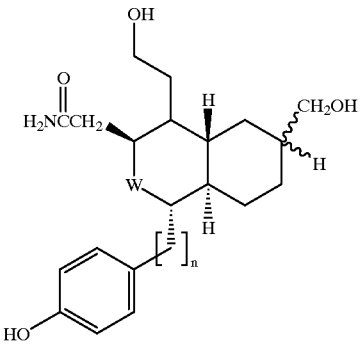

and enantiomers thereof.

23. A pharmaceutical composition for the inhibition of HIV infection which comprises
a compound of claim 1 in an amount effective for inhibition of HIV and a
pharmaceutically acceptable carrier.

24. A pharmaceutical dosage form for treatment of AIDS symptoms which comprises
an amount of a compound of claim 1 effective for inhibition of HIV infection.

25. A method for inhibition of HIV infection which comprises the step of administering a compound of claim 1 to an HIV-infected individual in an amount effective for inhibition of HIV.

26. A method for treatment of the symptoms of AIDS which comprises the step of administering a compound of claim 1 to an individual displaying said symptoms in an amount effective for inhibition of HIV.

27. A compound according to claim 1 having the formula:

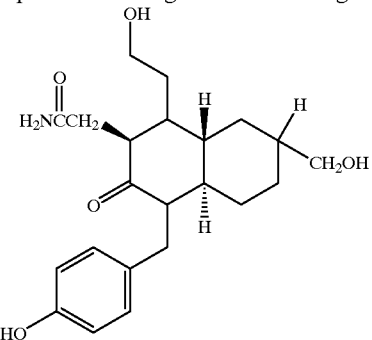

and enantiomers thereof.

28. A method for the treatment of the symptoms of AIDS which comprises the step of administering a compound of claim 19 to an individual displaying said symptoms in an amount effective for inhibition of HIV.

29. A method for the treatment of the symptoms of AIDS which comprises the step of administering a compound of claim 22 to an individual displaying said symptoms in an amount effective for inhibition of HIV.

* * * * *

UNITED STATES PATENT AND TRADEMARK OFFICE
CERTIFICATE OF CORRECTION

PATENT NO.    :  5,990,172                    Page 1 of 4

DATED         :  Nov. 23, 1999

INVENTOR(S)   :  Pincus et al.

It is certified that error appears in the above-identified patent and that said Letters Patent is hereby corrected as shown below:

On the cover page, column 1, under "FOREIGN PATENT DOCUMENTS" please rewrite "88/09338 12/1988    European Pat. Off." as --88/09338    12/1888    WO--.

At column 6, line 40, Formula X, please delete

"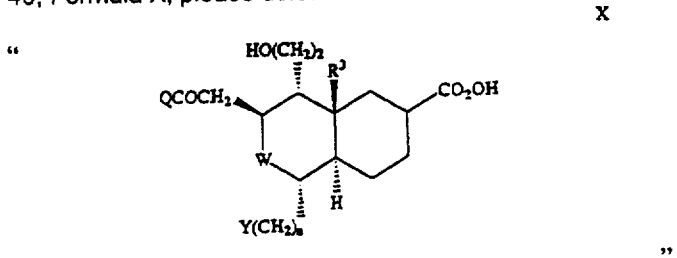"

and replace it with

--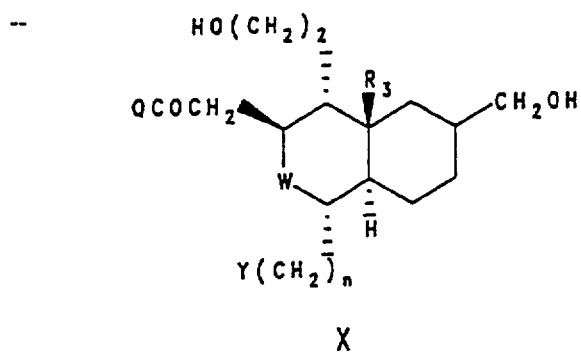--

UNITED STATES PATENT AND TRADEMARK OFFICE
CERTIFICATE OF CORRECTION

PATENT NO. : 5,990,172

DATED : Nov. 23, 1999

INVENTOR(S) : Pincus et al.

It is certified that error appears in the above-identified patent and that said Letters Patent is hereby corrected as shown below:

At column 7, lines 11 - 25, please delete

"

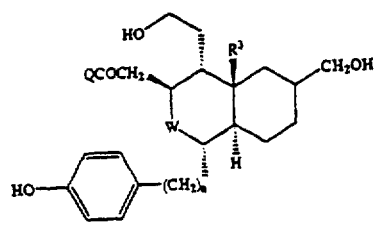

XI

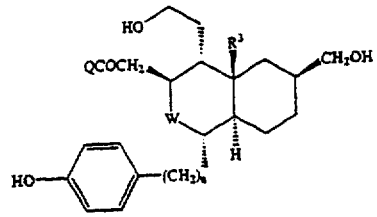

XIA

"

UNITED STATES PATENT AND TRADEMARK OFFICE
CERTIFICATE OF CORRECTION

PATENT NO. : 5,990,172

DATED : Nov. 23, 1999

INVENTOR(S) : Pincus et al.

It is certified that error appears in the above-identified patent and that said Letters Patent is hereby corrected as shown below:

and replace it with

--

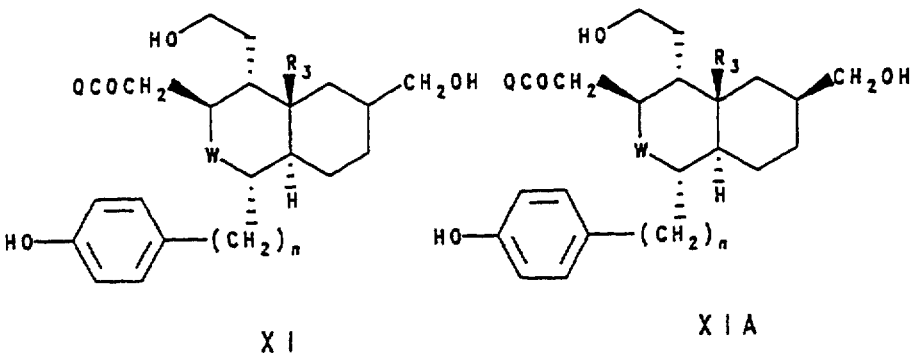

--

UNITED STATES PATENT AND TRADEMARK OFFICE
CERTIFICATE OF CORRECTION

PATENT NO.    :  5,990,172

DATED         :  Nov. 23, 1999

INVENTOR(S)   :  Pincus et al.

It is certified that error appears in the above-identified patent and that said Letters Patent is hereby corrected as shown below:

At column 14, line 23, please replace "benzylch (oromethyl" with --benzylchloromethyl--.
At column 17, line 44, please replace "$10_{-11}$" with --$10^{-11}$--.
At column 20, in Scheme 1, in the reagents between Formulas 2 and 3, please replace "1) MVK, TrltonB," with --1) MVK, Triton B,--.
At columns 23 and 24 in the scheme, in the reagents between formulas 6 and 15, please replace "1) Catechol borane THF, ClRh(PP$_3$)$_3$," with --1) Catechol borane THF, ClRh(PP$_2$)$_3$--.

Signed and Sealed this

Thirteenth Day of March, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 5,990,172
DATED : November 23, 1999
INVENTOR(S) : Pincus et al.

Page 1 of 1

It is certified that error appears in the above-identified patent and that said Letters Patent is hereby corrected as shown below:

<u>Column 42</u>:

Line 33, please replace "$(CH_2)_n$-" with --$(CH_2)_m$- --.

Signed and Sealed this

Twelfth Day of June, 2001

*Attest:*

*Nicholas P. Godici*

*Attesting Officer*

NICHOLAS P. GODICI
*Acting Director of the United States Patent and Trademark Office*